US009655631B2

United States Patent
Peterson et al.

(10) Patent No.: US 9,655,631 B2
(45) Date of Patent: May 23, 2017

(54) MILL HEAD FOR A BONE MILL, THE MILL HEAD HAVING ONE OR MORE CONTAINMENT RINGS THAT PREVENT UNWANTED DISCHARGE OF THE CONTENTS OF THE BONE MILL

(71) Applicant: Stryker Corporation, Kalamazoo, MI (US)

(72) Inventors: Michael Peterson, Portage, MI (US); Gary Kalinka, Wyoming, MI (US); Richard Burmeister, Kalamazoo, MI (US)

(73) Assignee: STRYKER CORPORATION, Kalamazoo, MI (US)

( * ) Notice: Subject to any disclaimer, the term of this patent is extended or adjusted under 35 U.S.C. 154(b) by 208 days.

(21) Appl. No.: 14/282,460

(22) Filed: May 20, 2014

(65) Prior Publication Data

US 2014/0257303 A1    Sep. 11, 2014

Related U.S. Application Data

(62) Division of application No. 13/667,078, filed on Nov. 2, 2012, now Pat. No. 8,746,600, which is a division
(Continued)

(51) Int. Cl.
*A61B 17/16* (2006.01)
*A61F 2/46* (2006.01)
(Continued)

(52) U.S. Cl.
CPC ........ *A61B 17/1615* (2013.01); *A61F 2/4644* (2013.01); *B02C 18/16* (2013.01);
(Continued)

(58) Field of Classification Search
CPC ......... A61B 17/1615; A61F 2002/4646; B02C 18/062; B02C 18/12; B02C 18/18;
(Continued)

(56) References Cited

U.S. PATENT DOCUMENTS 2,856,976 A   2/1955  MacDougal
4,095,751 A   6/1978  Artin
(Continued)

FOREIGN PATENT DOCUMENTS

EP   0 727 254 B2   9/2001
WO   2006/105950 A2   10/2006

OTHER PUBLICATIONS

EP "Search Report", Application No. 13 001 043.2 dated Apr. 2013.
(Continued)

*Primary Examiner* — David Bates

(57) ABSTRACT

A mill head for replaceable attachment to a base so as to collectively form a bone mill. The mill head includes: a first opening in which bone stock is introduced into the head; a cutting device that converts the bone stock into bone chips; a second opening through which the bone chips are discharged; and a third opening through which a motor integral with the base is attached to the cutting device. Internal to the mill head are containment rings. The containment rings prevent the discharge of material through the third opening. The containment rings are services the internal component of the mill head on which the cutting device rests.

44 Claims, 21 Drawing Sheets

Related U.S. Application Data of application No. 13/177,589, filed on Jul. 7, 2011, now Pat. No. 8,343,156, which is a division of application No. 11/936,448, filed on Nov. 7, 2007, now Pat. No. 8,002,774.

(51) Int. Cl.
*B02C 18/16* (2006.01)
*B02C 18/22* (2006.01)
*B02C 18/24* (2006.01)

(52) U.S. Cl.
CPC ............ *B02C 18/22* (2013.01); *B02C 18/24* (2013.01); *A61B 2017/1602* (2013.01); *A61F 2002/4645* (2013.01)

(58) Field of Classification Search
CPC ............ B02C 18/145; B02C 18/186; B02C 2018/188; A47J 43/14; A47J 43/16; A47J 43/18; A47J 43/20; A47J 43/26; A47J 43/32; A47J 43/255
USPC .................. 241/91, 92, 169.1, 273.2, 278.1
See application file for complete search history.

(56) References Cited

U.S. PATENT DOCUMENTS

| | | |
|---|---|---|
| 4,860,960 A | 8/1989 | Schwarz |
| 4,971,261 A | 11/1990 | Solomons |
| 5,397,068 A | 3/1995 | Solomons et al. |
| 5,662,282 A | 9/1997 | Meyer |
| 5,730,372 A | 3/1998 | Bradley |
| 5,918,821 A | 7/1999 | Grooms et al. |
| 5,924,357 A | 7/1999 | Chen |
| 6,287,312 B1 | 9/2001 | Clokie et al. |
| 6,318,651 B1 | 11/2001 | Spiering |
| 6,402,070 B1 | 6/2002 | Ishida et al. |
| 6,464,156 B1 | 10/2002 | Wexell |
| 6,481,652 B2 | 11/2002 | Strutz et al. |
| 6,484,954 B2 | 11/2002 | Lenox |
| 6,755,365 B1 | 6/2004 | Meredith |
| 6,814,323 B2 | 11/2004 | Starr et al. |
| 6,824,087 B2 | 11/2004 | McPherson et al. |
| 7,063,283 B2 | 6/2006 | Wanat |
| 7,131,605 B2 | 11/2006 | McPherson et al. |
| 7,156,329 B2 | 1/2007 | Hay et al. |
| 7,588,202 B2 | 9/2009 | Rasekhi |
| 7,891,591 B1 | 2/2011 | Hodgson et al. |
| 8,002,774 B2 | 8/2011 | Burmeister et al. |
| 2002/0040943 A1 | 4/2002 | Lenox |
| 2002/0063178 A1 | 5/2002 | Stru et al. |
| 2002/0070299 A1 | 6/2002 | Lenox |
| 2003/0226923 A1 | 12/2003 | Starr et al. |
| 2004/0000605 A1 | 1/2004 | McPherson et al. |
| 2005/0178866 A1 | 8/2005 | Mauch et al. |
| 2005/0194484 A1 | 9/2005 | Starr |
| 2005/0207273 A1 | 9/2005 | Newman et al. |
| 2005/0236502 A1 | 10/2005 | Anderson et al. |
| 2006/0138260 A1 | 6/2006 | Hay et al. |
| 2007/0164137 A1 | 7/2007 | Rasekhi |
| 2010/0004653 A1 | 1/2010 | Rasekhi et al. |

OTHER PUBLICATIONS

"Leibinger Bone Mill", Jun. 2006, 13 photographs, Jun. 7, 2006.
PCT App. No. PCT/US2008/082348 "International Search Report and Written Opinion", Mar. 2009.

MILL HEAD FOR A BONE MILL, THE MILL HEAD HAVING ONE OR MORE CONTAINMENT RINGS THAT PREVENT UNWANTED DISCHARGE OF THE CONTENTS OF THE BONE MILL

This application is a divisional of U.S. patent application Ser. No. 13/667,078 filed 2 Nov. 2012 now U.S. Pat. No. 8,746,600. Patent application Ser. No. 13/667,078 is a divisional of U.S. patent application Ser. No. 13/177,589, 7 Jul. 2011 now U.S. Pat. No. 8,343,156 B2. Patent application Ser. No. 13/177,589 is a divisional of U.S. patent application Ser. No. 11/936,448 filed 7 Nov. 2007 now U.S. Pat. No. 8,002,774. The applications from which this application now claims priority are incorporated by reference herein.

FIELD OF THE INVENTION

This invention relates generally to a bone mill used to reduce the size of bone used in surgical procedures. More particularly, this invention is generally related to a bone mill that includes a base and a mill unit that is removably attached to the base.

BACKGROUND OF THE INVENTION

A bone mill is a medical device that, as its name implies, reduces the size of section of bone. The milled bone, which is often chip sized, is used in a medical procedure as a filler adjacent other sections of bone. For example, in a spinal fusion procedure, it is a known practice to place a compound formed out of milled bone around the rods used to hold adjacent vertebra in alignment. This compound serves as a lattice upon which the tissues forming the vertebra grow so as to form a bone-link between these vertebras. This link minimizes the load imposed on the rods. Milled bone is similarly used as filler and/or growth formation lattice in orthopedic surgical procedures and other procedures such as maxillofacial procedures.

Milled bone is used as a filler/growth formation lattice in these procedures because the material, the proteins from which it is formed can serve as make-up material from which the blast cells of the adjacent living bone cells can form new bone. Accordingly, in a surgical procedure in which it is desirable to foster the growth of new bone, milled bone, to which supplemental material is sometimes added, is employed as filler in the spaces in which bone growth is desired.

Milled bone is formed by taking a large mass of bone, a mass that may have a volume of 8 $cm^3$ or more, and reducing it into chips. A chip typically occupies of volume of 0.008 $cm^3$ or smaller.

The bone mill is the device used to mill, morsellize, the large mass of bone to chip size. A typical bone mill includes a housing. A blade assembly or mill head is rotatably mounted to the housing. This blade assembly/mill head is formed with cutting surfaces able to shave or break up the bone pressed against it. There is also some type of device for driving the blade assembly/mill head. If the bone mill is manually operated, the drive device is often a handle capable of rotating the blade assembly/mill. A powered bone mill includes a motor that performs this function.

A bone mill, it should also be understood, is typically designed to be used in the operating room in which the procedure is being performed for which the bone chips are required. This is because, in many situations, the bone used to form the bone chips comes from another portion of the patient's body. The use of the patient's own tissue reduces the likelihood of its rejection by the body. Therefore, an initial part of procedure in which the bone compound is used often involves harvesting a small piece of bone from another portion of the patient's body. This bone is milled into the compound-forming bone chips. This bone harvested from the patient is referred to as autograft bone. Bone from a source other than the patient is referred to as allograft bone.

Ideally, the compound-forming bone chips should undergo as minimal as possible surface oxidation prior to implantation in the body. This surface oxidation results reduces the extent to which the material forming the bone chips can serve as lattice or feedstock that fosters the growth of new bone. Thus, even when allograft bone is milled to form bone chips, this milling process is performed as close as possible to the time at which the chip compound is needed.

Known bone mills work reasonably well. Nevertheless, there are some limitations associated with these devices. Some bone mills, for example are provided with reusable blades/mill heads. One disadvantage of this type of assembly is that after each se, time must be spent to disassembly its components for cleaning and then reassemble them for later use. A further disadvantage of this type of device is that a blade/mill head typically has a number of closely spaced apart surfaces some of which have sharp edges. After each use of the device, care must be taken to carefully sterilize the blade. This process can take an appreciable amount of time in order to ensure both that the blade is properly sterilized and the person perform this task does not cut his/her fingers on the sharp edges.

Furthermore, over time, the blades of a reusable mill invariably dull. This requires one to either by a new blade set or resharpen the existing blades.

To avoid the difficulties associated with sterilizing a bone mill blade, bone mills with use once, replaceable, mill units are available. This type of device includes a base to which a mill unit is removably attached. The mill unit includes a body in which a blade is rotatably mounted. Often the base includes a motor for driving the blade. This type of device is designed so that, after a single use, the mill unit is discarded. An advantage of this type of device is that medical personnel do not have to concern themselves with sterilizing, the blade, a sharp metal object.

Some of these systems are designed so that once the bone is morsellized, the medical personnel have to use either instruments or their fingers to remove the bone from around the blade. Having to perform this step adds to the overall time it takes to provide the bone. Some known disposable bone mills are designed so that in order to access the bone chips, the medical personnel have to remove the blade. In this step of the procedure, personnel have to concern themselves with not getting cut by a sharp metal object.

Further, many known bone mills are constructed so that the blade may repeatedly strike against the same surface of the bone or bone chip. The frictional heat generated by such activity can damage the material forming the bone. This damage can adversely affect the ability of the bone chips to function as growth material for the new bone.

Still another disadvantage of some known bone mills is that frequency with which the bone milled is reduced in size in the milling process varies within a single milling operation. Some bone may be subjected to only nominal milling. The chips formed as a consequence of this milling may be tool large to be used in the subsequent procedure. Still other bone, in the same milling operation, may, as a result of repetitive milling, be milled to down to very small, almost dust sized particles. The small size of these chips makes their collection for use in the procedure difficult.

Moreover, a sizeable fraction of the bone milled by some bone mills is often not easily accessible for use. This is especially the situation when autograft bone is used to form the bone chips. This particular bone tends to be moist. Consequently, the bone chips have been known to adhere to surfaces of the bone mill, including the actual blade. To ensure that enough bone chips formed from freshly harvested bone is available for use, medical personnel may sometimes feel obligated to form an excess amount of chips knowing that some will not be available for use. Alternatively, these personnel may, once the milling process is completed, have to carefully remove the adhered bone from the surfaces of the mill including the surfaces around the sharp cutting edges of the blade.

SUMMARY OF THE INVENTION

This invention is directed to a new and useful bone mill. The bone mill of this invention includes a base and a mill head that is removably attached to the base. Internal to the base is a motor. Internal to the mill head is rotating cutting disc. Mounted to the mill head is a movable plunger. Also attached to the mill head and aligned with plunger is a catch tray.

To use the bone mill of this invention, the bone mill head is mounted to the base. The motor rotates the cutting disc. The plunger is depressed to press the bone against the cutting disc. As a consequence of the rotation of the cutting disc, the disc cuts the bone so as to form chips. The chips fall into the catch tray. The chips are then readily accessible for use by removal of the catch tray.

The mill head of this invention has features that minimize the extent to which the formed bone chips adhere to the cutting disc and the other surfaces of the mill head. These features thus ensure, to a significant extent that the chips formed by the mill head enter the catch tray so they can be used in the procedure.

Still another feature of the bone mill of this invention is that once a chip is cut from the bone, it does not again strike the cutting disc. This minimal contact with the cutting disc reduces the likelihood that frictional heat such contact can generate will damage the chip.

Further, the base and mill head are constructed so that the seating of the head to the base results in the auto engagement of the cutting disc to the drive spindle integral with the motor. This engagement occurs even if the disc is not precisely aligned with the spindle. This feature of the bone mill of this invention contributes to minimizing the costs associated with providing the mill head.

BRIEF DESCRIPTION OF THE DRAWINGS

The invention is pointed out with particularity in the claims. The above and further features and benefits of the bone mill of this invention are better understood by the following Detailed Description taken in conjunction with the accompanying drawings in which:

DETAILED DESCRIPTION

I. Overview

Figure 1:
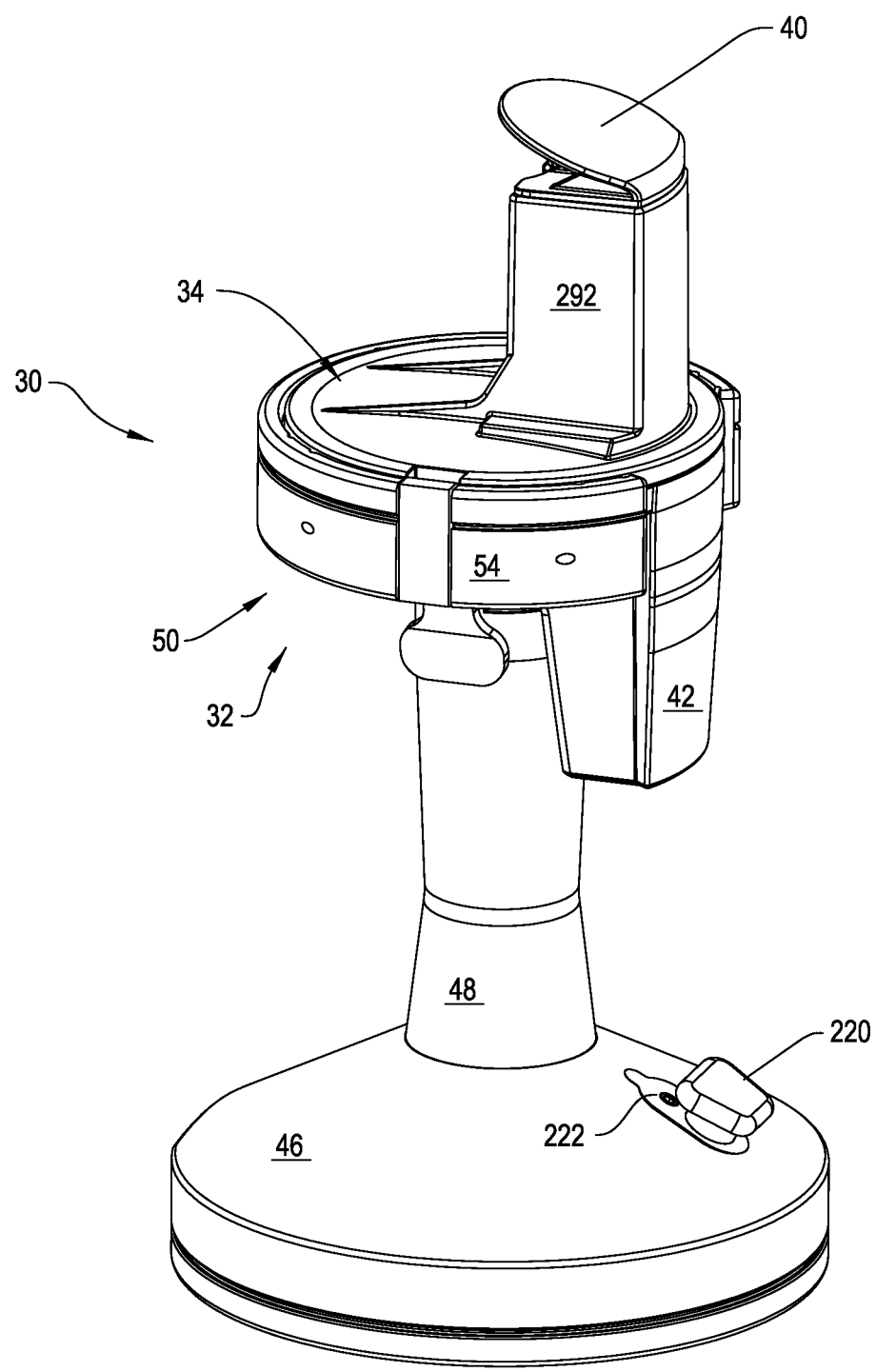
FIG. 1 is a perspective view of a bone mill of this invention.
Figure 2:
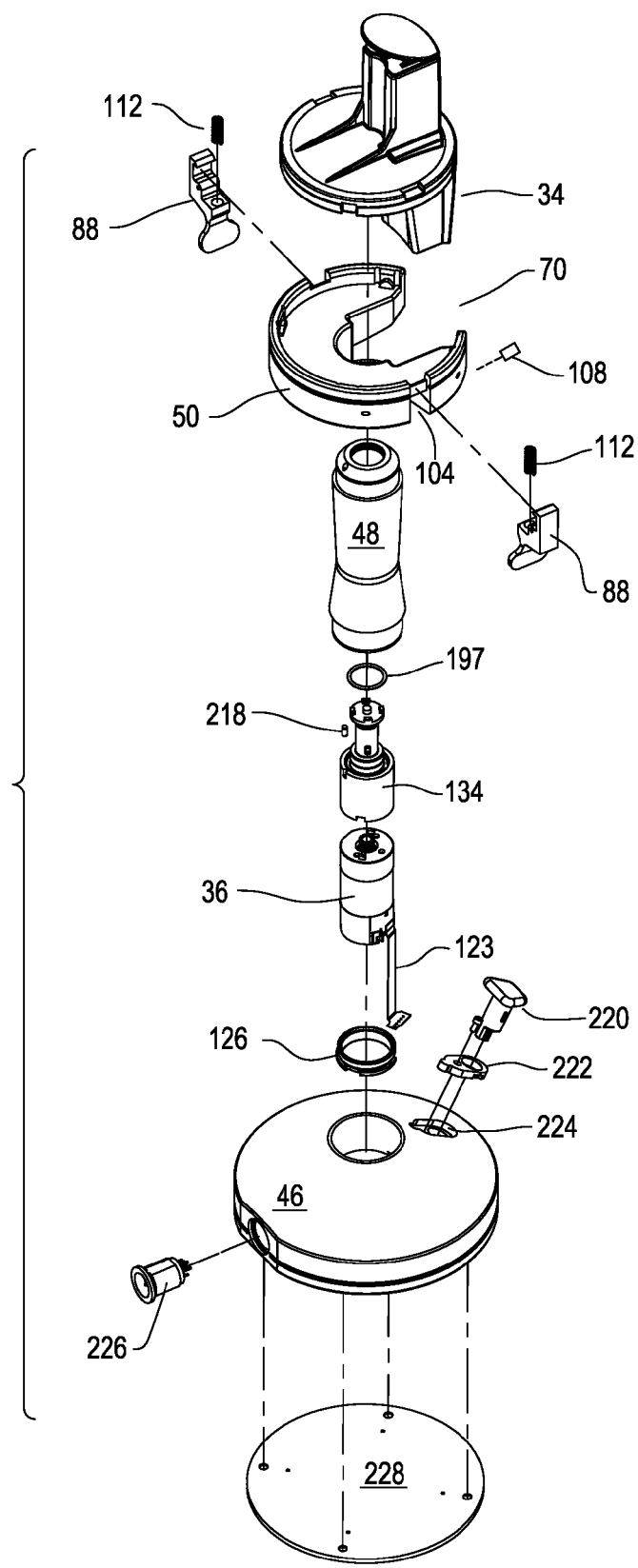
FIG. 2 is an exploded view of the mill base.

As seen by reference to FIG. 1 a bone mill 30 of this invention includes a base 32 to which a mill head 34 is removably attached. Internal to the base 32 is a motor 36 (FIG. 2). A generally planner shaped cutting disc 38 (FIG. 18) is disposed inside the mill head 34. A plunger 40 is mounted to the top of the mill head 34. Disposed below the plunger 40, below the underside of the cutting disc 38 is removable catch tray 42. Bone mill 30 is used by actuating the motor 36 so that the motor rotates disc 38. Plunger 40 is used to press bone against the rotating disc 38 so as to result in the formation of bone chips. These chips fall into catch tray 42 so that the chips are available for use in a surgical procedure.

II. Base

The base 30, as seen in FIGS. 1 and 2, includes a circular foot 46. A leg 48, having a circular cross section, extends upwardly from foot 46. In the illustrated version of the invention, the top of the foot 46 has a frusto-conical, inwardly tapered profile such that leg 48 extends upwardly from the top center of the foot. The leg 48 has a diameter less than the diameter of the foot 46.

Leg 48 is formed of metal such as aluminum, stainless steel or plastic. In the illustrated version of the invention, while the leg 48, seen best in FIG. 3, has a circular cross sectional profile along the whole length of the leg, the diameter of the leg is not constant. Specifically, the diameter of the leg 48 tapers inwardly for the first 25% of the along the leg from the top of the foot 46. Above this point, the diameter of the of the leg 48 tapers outwardly along the remaining length of the leg. In the illustrated version of the invention, leg 48 has a slightly smaller diameter at the top than at the bottom. A bore 47 extends axially through leg 48. Bore 47 has a number of contiguous sections each with a diameter different than that of the adjacent section(s). At the top end of the leg 48, the leg is formed to have an annular inwardly directed lip 49. Lip 49 defines the top end opening into bore 47.

A pedestal 50 is disposed on top of the leg 48. The pedestal 50, best seen in FIGS. 4 and 5, has a generally circular cross sectional profile. In the illustrated version of the invention, pedestal 50 has a bottom surface 52 that tapers outwardly from the top of the leg 48. An arcuate side wall 54 extends upwardly the top of the bottom surface 52. Base 32 of the illustrated version of the invention is formed so that the pedestal side wall 54 defines a circle that has a diameter less than that of maximum diameter of the foot 46 and greater than the widest diameter section of the leg 48.

The upper portion of the pedestal side wall 54 is part of an arcuate lip 56 that extends around the perimeter of the pedestal 50 and that projects above the surrounding top surface 58 of the pedestal. Lip 56 and top surface 58 thus define above the top of the pedestal 50 a recess 60. Recess 60 is the void space in which mill head 34 seats when mounted to base 32.

Figure 3:
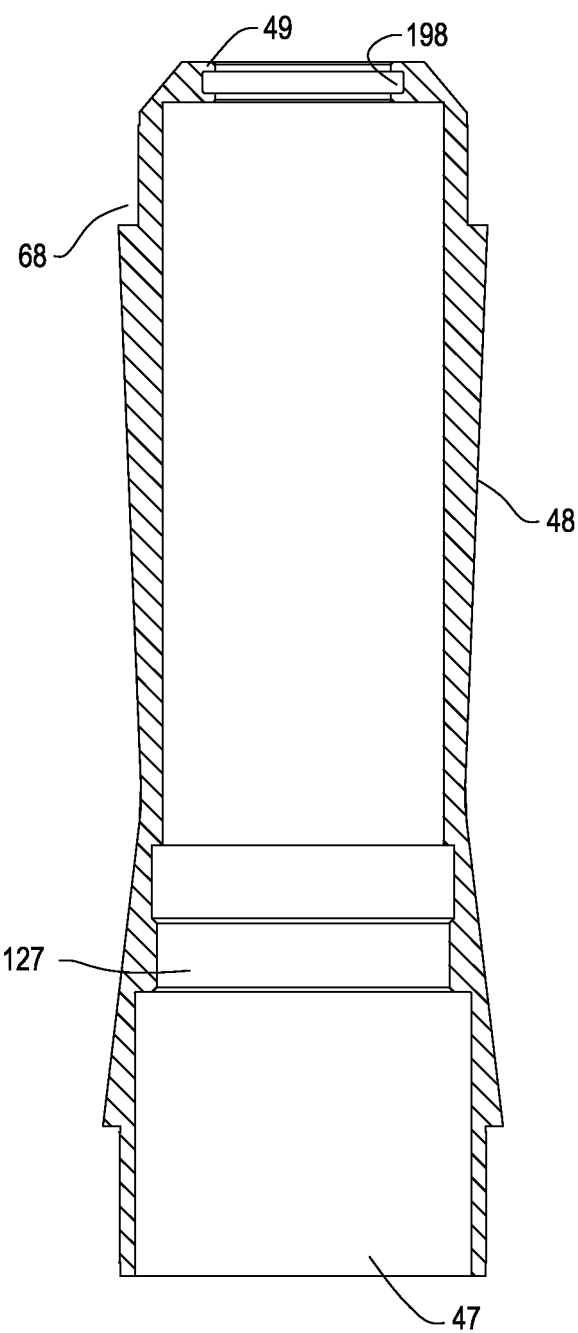
FIG. 3 is a cross sectional view of the base leg.

Pedestal 50 is also shaped to define a through opening 64 that is centered on the longitudinal axis of the pedestal. In the illustrated version of the invention, integrally formed with pedestal 50 is an annular skirt 66 that extends downwardly from the pedestal bottom surface. The inner surface of skirt 66 defines opening 64. When base 30 is assembled, the pedestal skirt 66 is disposed over an adjacent inwardly stepped surface 68 of leg 48 (FIG. 3). Pedestal skirt 66 is press fit to the top of the leg.

The pedestal 50 is further formed to define a notch 70. Notch 70 projects outwardly from opening 64 to the outer perimeter of the pedestal 50. Notch 70 is defined, in part, by two parallel inner side surfaces 72 in the body of the parallel (one surface 72 identified in FIG. 5). Inward of lip 56, each inner side surface 72 terminates at an outer side surface 74 that angles outwardly away from the associated inner side surface 74. Outer side surfaces 74 thus define the outer perimeter of notch 70. The outward flare of the opposed outer side surfaces 74 provide notch 70 with a shape, adjacent the outer perimeter of the pedestal 50 that is inwardly tapered. Inward of the outer side surfaces 74, parallel inner side surfaces 72 provide notch 70 with a rectangular shape.

Pedestal 50 is further formed to have a number of arcuately spaced apart teeth 80 that are disposed around and extend upwardly from the outer perimeter of the pedestal top surface 58. Each tooth 80 is disposed against the inner arcuate surface of lip 54. In some versions of the invention, teeth 80 are integrally formed with the inner arcuate surface of lip 54. Each tooth 80 is shaped to have a top, a crown, with a top surface 82 from which two lateral surfaces 84 extend diagonally downwardly. In the illustrated version of the invention semi-circular grooves are formed in the lip 54 on either side of each tooth 80 (grooves not identified). These grooves are present for manufacturing purposes and are otherwise not material to this invention.

Figure 6:
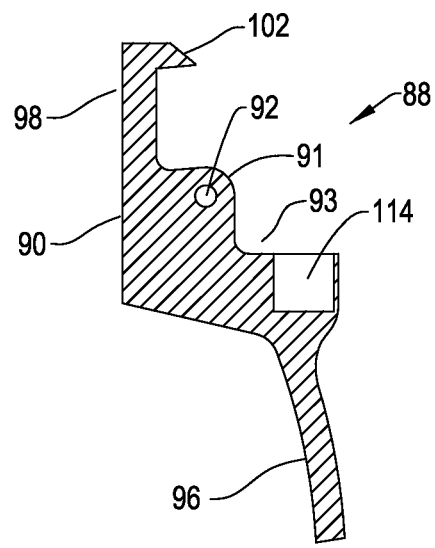
FIG. 6 is a cross sectional view of a retention arm used to releasably hold the mill head to the base.

A pair of retention arms 88 that are pivotally mounted to the pedestal 50 releasably hold the mill head 34 to the base 32. Each retention arm 88, as seen in detail in FIG. 6, includes a solid base 90 with a generally polygonal shape. While the corners of the base 90 are generally angular, the top inner corner surface 91 of the base 90, the corner directed to the top and center of the pedestal, is rounded. Inward of surface 91, arm base is formed with a bore 92. A ledge 93 extends inward from the inner side of the arm base 90. The ledge 93 has a height less than that of the base 90. A lever 96 extends downwardly from the bottom surface of the arm ledge 93. Each arm 88 is further formed to have a finger 98 that extends upwardly from the outer top surface of the base 90. The finger 98 is hook shaped such that at the top of the finger there is an inwardly directed tab 102 that extend a short distance of the top surface of the arm base 88.

Each retention arm 88 is operated in a cut-out space 104 defined in the pedestal 50. Each cut-out space 104 is formed, in part, by breaks in the pedestal bottom surface 52 and sidewall 54 shaped to define separate contiguous void spaces in which the arm base 90 and ledge 93 are seated. Each cut-out space 104 is further formed in part by a break in the outer perimeter of the pedestal lip 56 in which arm finger 98 is seated. Integral with the cut-out spaces 104 are notches in the top of the lip 54 in which the finger tabs 102 seat (notches not identified). Retention arms tabs 102 project into the top of pedestal recess 60.

Figure 5:
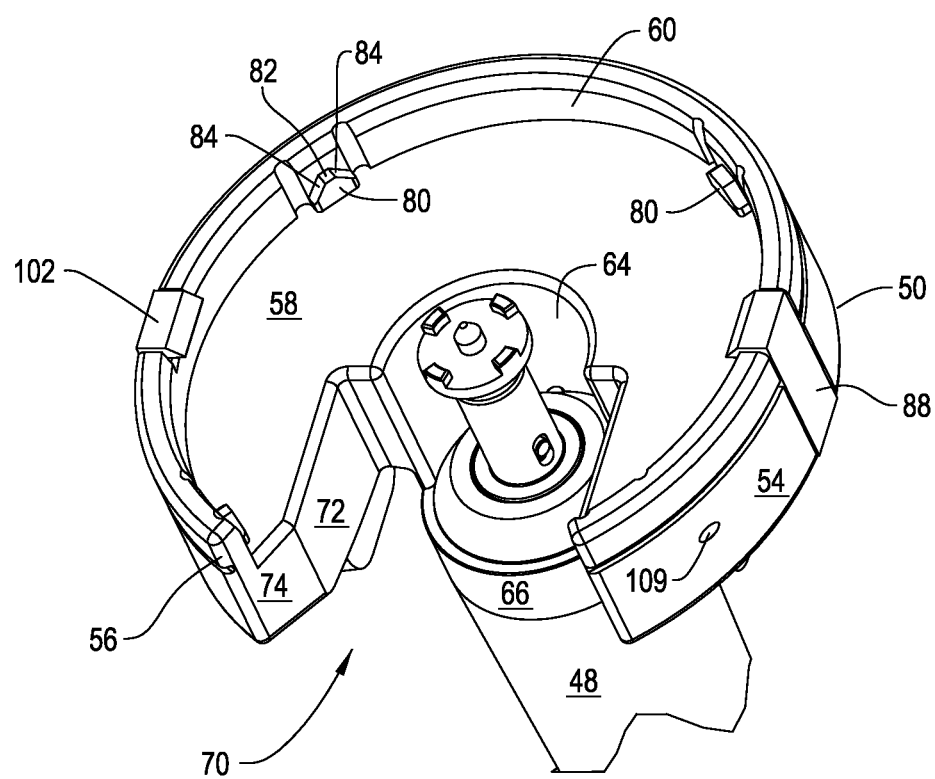
FIG. 5 is a perspective view of the top of the base.

A pivot pin 108, one seen in FIG. 2, rotatably holds each retention arm 88 to the base pedestal 50. Each pin 108 extends through the bore 92 in the inner upper corner of the associated arm base 90. The opposed ends of the pin 108 are disposed in bore 109 formed in the pedestal 50. (The opening into one of the pin bores 109 is seen in FIG. 5.) Each pin bore 109, it should be appreciated is intersected by the cut-out space 104.

Coil springs 112 (FIG. 2) mounted to the pedestal 50 normally hold each retention arm 88 in the locked state. Each coil spring 112 has a first end disposed in a closed-ended, downwardly opening bore 114 formed in the pedestal 50. Each bore 114 opens into the cut-out space 104 for the associated arm 50. The opposed end of each spring 114 seats on an upwardly directed surface of the ledge 93 of the associated arm 88. Thus, each spring 112 exerts a force on the associated arm that positions the arm so that the tab 102 normally seats in the top located pedestal recess 60. As a result of the biasing of the arm by spring 112, it will further be appreciated that each arm level 96 is normally downwardly directed so as to be generally aligned with base leg 48.

Figure 4:
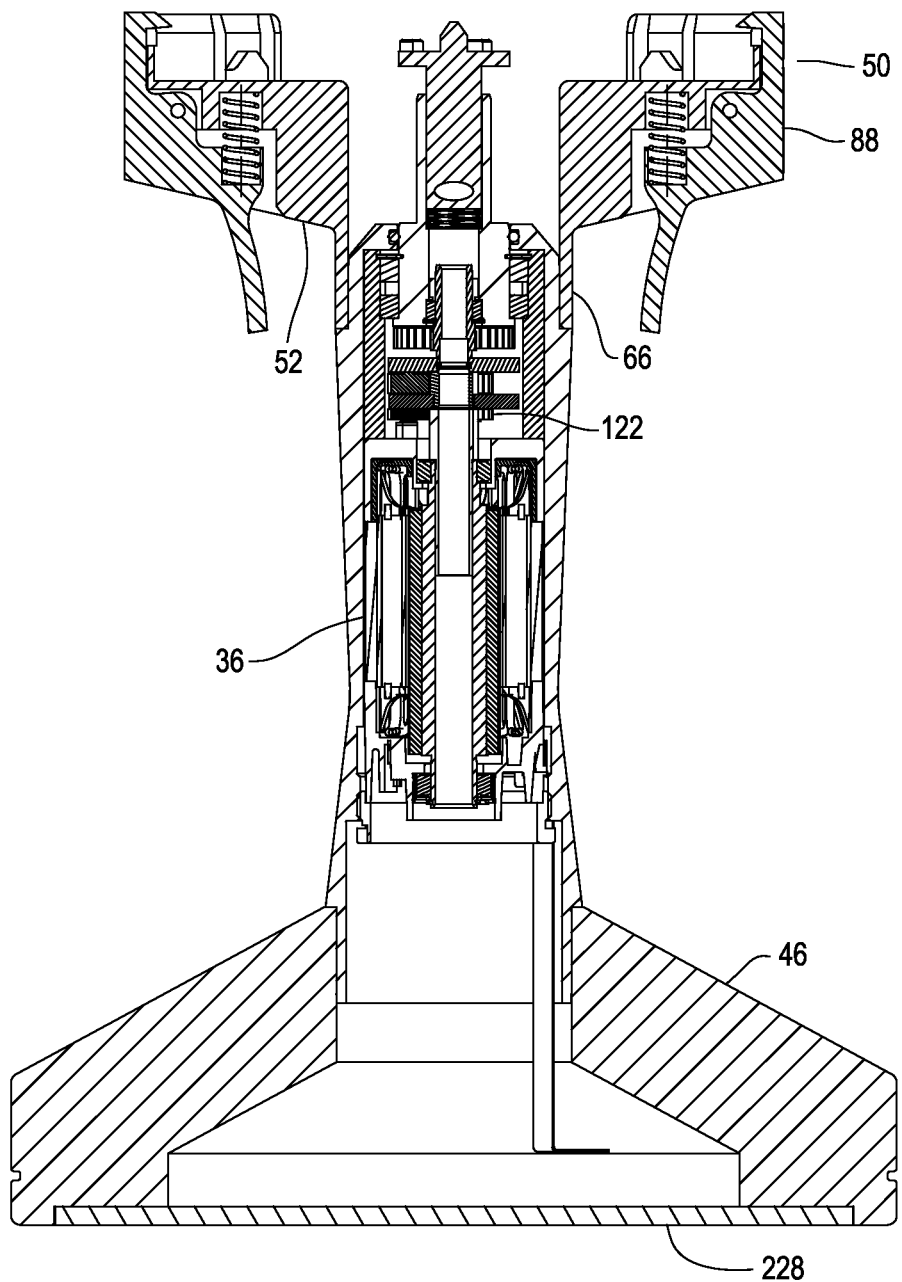
FIG. 4 is a cross sectional view of the base.

The base motor 36, now described by reference to FIGS. 2 and 4, is disposed in leg bore 47. In one version of the invention, the motor 36 is the motor employed in the Applicant's Assignee's ES6 Surgical Sagittal Saw. This motor is a four-pole, three-phase motor. This particular motor is capable of a no-load maximum shaft speed of at least 20,000 RPM. The motor 36 is disposed in the leg 48 so as to be suspended in the leg 48 above foot 46. Motor 36 has an output shaft (not illustrated) to which a gear head 122 is attached. Extending downwardly from the motor 36 is a flex circuit 123. Flex circuit 123 carriers the conductors over which the motor windings are selectively tied to ground and a voltage source. The flex circuit 123 also supports the conductors over which the signals from the Hall sensors internal to the motor are output, over which a 5VD is supplied to the motor (the Halls) and a ground connection is obtained.

The outer perimeter of motor 36 rests on a ring 126 screw secured inside the leg 48. The ring is threaded into a section 127 of leg bore 47 (FIG. 3). Ring 126 is formed with slots 128 located around the outer perimeter of the ring. When base 32 is assembled, the flex circuit 123 extending from the motor 36 is disposed within ring 126.

Figure 7A:
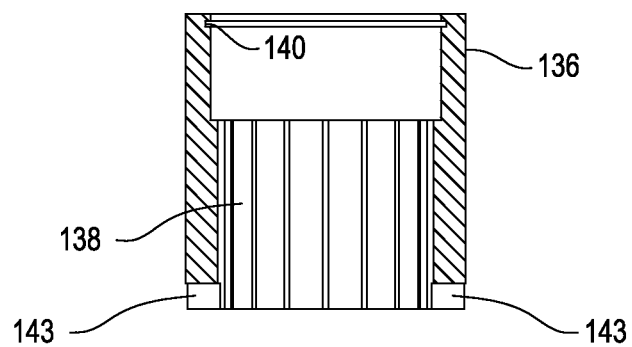
FIG. 7A is a cross sectional view of the housing, the ring gear, of the gear train.

A gear train 134 is disposed in hollow of leg 48 so as to be disposed over motor 36. The gear train 134, best seen in FIGS. 7 and 8, includes a set of planetary gear assemblies that reduce the speed/increase the torque of the rotational moment produced by motor 36. Specifically, gear train 134 includes a tube like housing 136, best seen in FIG. 7A, that functions as the ring gear for the individual planetary gear assemblies. Housing 136 has a smooth outer wall and is designed to closely slip fit into the hollow bore of leg 48. The gear train housing 136 is formed so that the lower inner circumferential wall has arcuately spaced apart teeth 138. Above teeth 138 housing 136 is formed to have an inner diameter that is greater than the inner diameter of the void space formed by the toothed portion of the housing. Immediately below the top of the housing 138, the housing is formed to have a groove 140 that extends circumferentially around the inner wall of the housing. Gear train housing 136 is further formed so as to have a semi-circular channel 142 that extends downwardly from the top of the housing along the outer surface. Channel 142 extends longitudinally along the housing for distance that is approximately 15% of the overall length of the housing.

The bottom of the gear train housing 136 is formed with two diametrically opposed notches 143. Notches 143 are provided to receive a tool used to facilitate the insertion/removal of the gear train 134 from leg bore 47. Further, when the base 32 is assembled tabs integral with the motor (tabs not illustrated) seat in the notches 143. The engagement of these tabs with the gear train housing 136 blocks rotation of the motor 36.

Disposed within the gear train housing 136 are three planetary gear assemblies. The first planetary gear assembly includes a carrier disk 146. Three gears 148 (two shown in FIG. 7) are rotatably mounted to the underside of the carrier disk 146, the side directed to motor 36. Gears 148 are equangularly spaced apart from each other. Gears 148, like the gears 154 and 182 of, respectively, the second and third planetary gear assemblies are mounted to the carrier disc 146 so that the teeth of the gears 148 will engage the gear housing teeth 138. When base 32 is assembled, gears 148 also engage the gear head 122 of motor 36. A center gear 150 is fixedly mounted to the top side of carrier disk 146. Center gear 150 is coaxial with disk 146.

A second carrier disk, disk 152, forms part of the second planetary gear assembly. Rotatably mounted to the underside of disk 152 are three equangularly spaced apart gears 154. Gears 154 are sized and positioned to engage both center gear 150 and gear train housing teeth 138. A tubular stem 156 extends upwardly from the top surface of carrier disk 152 and is coaxial with the disk 152. Stem 156 is formed to define a gear 158 that is located above the surface of center disk 152.

Figure 9:
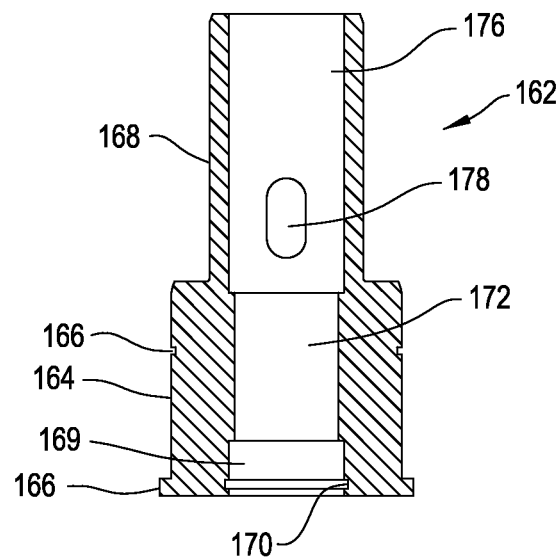
FIG. 9 is a cross sectional view of the drive coupler of the gear train

The third planetary gear assembly includes a multisection drive coupler 162 described best by reference to FIG. 9. Drive coupler 162 is shaped to have a cylindrical base 164. At the bottom end of the base a small annular step 166 projects radially outwardly from the perimeter of the base of the base. A short distance from the top of the base 164, drive coupler 162 is formed to have an annular groove 167. Groove 167 extends circumferentially around the outer surface of the base 164. Formed integrally with and extending above the base 164, drive coupler 164 is shaped to have a stem 168. Stem 168, while concentric with base 164 has a diameter less than that of the base.

Drive coupler 162 is further formed to have three coaxial contiguous bores that form a through opening, end-to end, centered along the longitudinal axis of the coupler. A first bore, bore 169 in FIG. 9, extends from the bottom of the coupler through the longitudinal slice subtended by step 166 and a section of the base 164 above the step. Immediately above the open end of bore 169, the drive coupler 164 is formed to define an annular groove 170 in the interior wall that defines bore 169. Contiguous with and located above bore 169, the drive coupler 162 is formed to define a second bore, bore 172. Bore 172 extends upwardly from bore 169 to just below the top of the coupler base 164. Bore 172 has a diameter slightly less than that of bore 169. Both bores 169 and 172 are greater in diameter than stem 156 integral with the second planetary gear assembly. Above bore 172, drive coupler 162 is formed to have a third bore, bore 176. Bore 176 extends from bore 172, through the top of the coupler base 164 and the whole of the stem 168. The open end of bore 176 thus forms the top end opening into drive coupler. Bore 176 has a diameter greater than that of bore 176.

The drive coupler 162 is further formed to have two diametrically opposed oval openings 178. Openings 178 are formed in the stem 168 above where the stem emerges from the base 164. Openings 178 have longitudinal axes parallel to the longitudinal axis of the drive coupler 162. The openings 178 thus are contiguous with bore 176.

Figure 7:
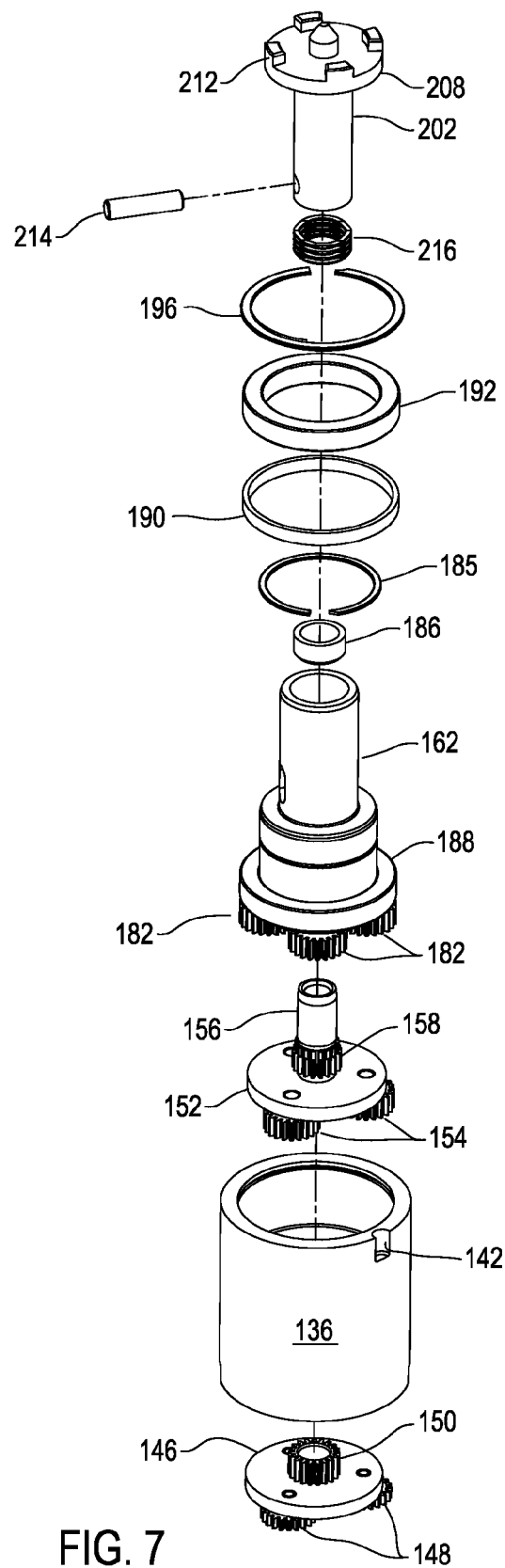
FIG. 7 is an exploded view of the gear train internal to the base.
Figure 8:
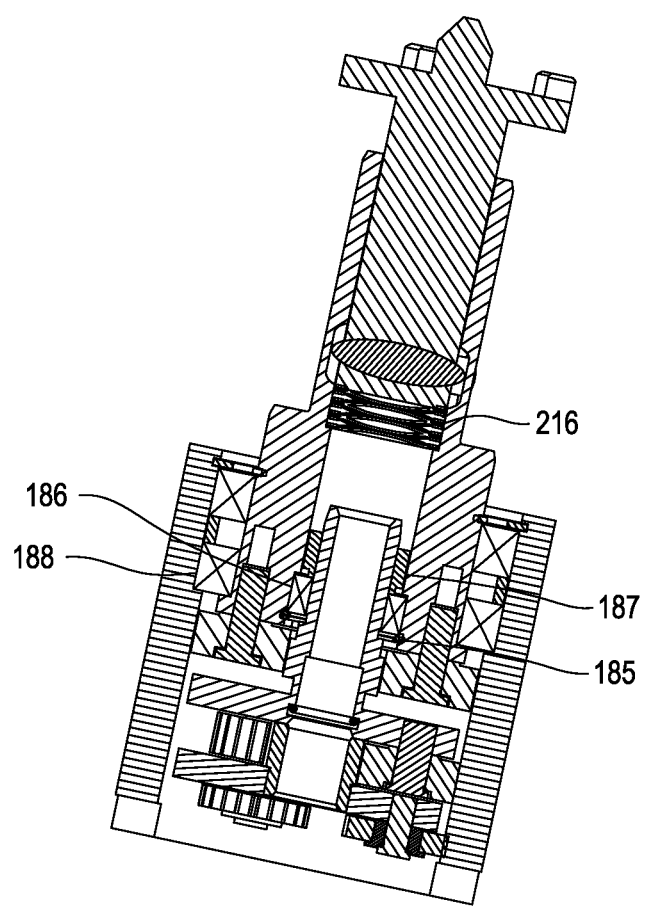
FIG. 8 is a cross section view of the gear train.

The third planetary gear assembly has four planet gears 182, (three seen in FIG. 7). Planet gears 182 are mounted to the undersurface of drive coupler base 164. Planet gears 182 are sized and position to engage 158 of the second planetary gear assembly and housing teeth 138.

When gear train 134 is assembled, the second planet gear assembly is positioned so that stem 156 is disposed with drive coupler bores 169 and 172. A bearing assembly 186 provides a low friction coupling between the stem 156 and the drive coupler 162. The outer race of bearing assembly 186 is seated in the outer perimeter of the drive coupler bore 169. At least one snap ring 185 disposed in drive coupler groove 170 holds the bearing assembly 186 in bore 169. The inner race of the bearing assembly 186 is disposed about the outer surface of stem 156 above gear 158. A sleeve 187 formed from stainless steel is press fit over stem 156 above bearing assembly 186. Sleeve 187 has a lip, not identified that abuts the upper exposed inner race of the bearing assembly 187. Sleeve 187 thus blocks the removal of carrier disc 152 from the drive coupler 162.

Two bearing assemblies 188 and 192 rotatably hold the drive coupler 164 to the gear train housing 136. The outer races of both bearing assemblies 188 and 190 are disposed against the smooth inner wall of the gear train housing 136; the inner races are disposed against the outer circumferential wall of the drive coupler base 164. A first one of the bearing assemblies, assembly 188, is positioned so that the outer race of the assembly seats on the step defined by tops of the housing teeth 138. The inner race of bearing assembly 188 is seated against the drive coupler step 166.

A ring shaped spacer 190 separates bearing assemblies 188 and 192. Spacer 190 is disposed against the smooth inner wall of the gear train housing. Spacer is sandwiched between the outer races of both bearing assemblies 188 and 192.

A retaining ring 196 is snap fitted in groove 140 internal to the gear train housing 134. Retaining ring 196 extends over the outer race of the bearing assembly 192. Retaining ring 196 thus holds bearing assembly 192 and the components disposed below the assembly 192 in the gear train housing 136.

Figure 10:
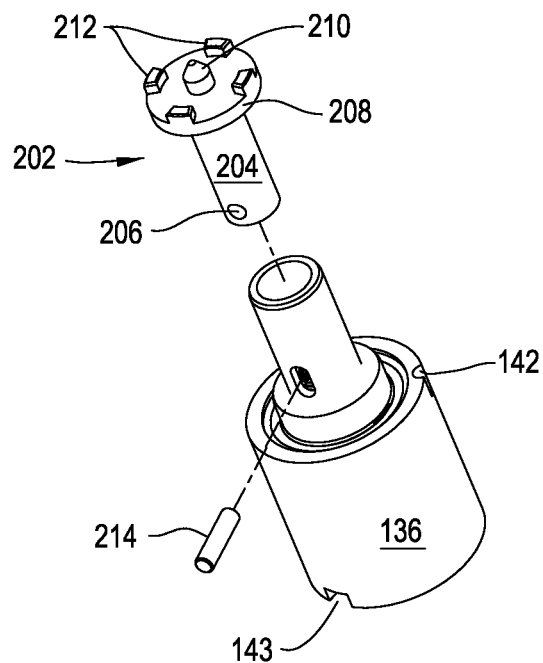
FIG. 10 is an exploded view illustrating the relationship of the spindle to the gear train.

A spindle 202, now described by initial reference to FIG. 10, extends from the drive coupler 162 and transfers the torque developed by the motor 36 to the mill cutting disc 38. Spindle 202 is shaped to include a generally solid post 204. Post 204 has a diameter that allows it to slidably fit in bore 176 internal to the drive coupler stem 168. Post 204 is formed to have a laterally extending through bore 206.

Above the post 204, spindle 202 is shaped to have a disc-shaped head 208. The spindle 202 is formed so that head 208 has a diameter approximately equal to that of the drive coupler base 164. A number of different components extend upwardly from the top surface of the spindle head 208. One of these components is an alignment pin 210. The alignment pin 210 is coaxial with the longitudinal axis of the spindle 202; the pin 210 extends upwardly from the center of the head. Pin 210 is shaped so that the lower portion, the portion that extends upwardly from the spindle head 208, has a cylindrical shape. The top portion of alignment pin has a shape of a cone with a flattened tip. (The individual sections of alignment pin 210 are not identified.)

Four equangularly spaced apart alignment teeth 212 also extend upwardly from the top surface of the spindle head 208. The teeth 212 are located around the outer perimeter of the spindle head 208. The arcuate outer surfaces of teeth 212 are flush with the outer surface of the spindle head 208. Each tooth has a pair of inwardly tapered side surfaces and an arcuate inner surface. (Surfaces not identified.) The radius of curvature of the inner surfaces of each tooth 212 is less than the radius of curvature of the outer surface. Teeth 212 do not extend as far above the spindle head 208 as does alignment pin 210.

Spindle 202 is positioned so that post 204 is slidably mounted in the drive coupler stem bore 176. A pin 214, extends through spindle bore 206. The opposed ends of the pin 214 are seated in the oval openings 178 formed in drive coupler stem 168. Pin 214 thus holds the spindle 202 to the drive coupler 162 so that the spindle rotates in unison with the drive coupler and is able to move longitudinally relative to the drive coupler.

A spring 216 is disposed in the drive coupler 162 below spindle 202. Spring 216 is a wave spring. One end of spring 216 is seated on the annular step internal to the drive coupler between bores 172 and 176. The opposed end of spring 216 is disposed against the bottom end of spindle post 204. Spring 216 is selected so to exert an upward bias on spindle post 204. Thus force, which can be overcome by the application of manual force, serves to normally urge the spindle head 208 away from the drive coupler 162.

When gear train 134 is mounted in leg 48, an anti-rotation pin 218 is seated in the channel 142 formed in gear train housing 136. The exposed portion of pin 218 seat in a complementary groove formed in the interior wall of the leg 48 that defines the section of leg bore 47 in which the gear train is seated (groove not illustrated). Anti-rotation pin 218 thus inhibits the rotational movement of the gear train housing 136.

In some versions of the invention, the motor 36 and gear train 134 are collectively provided so that the spindle 202, and by extension, the cutting disc 38 are able to rotate at speeds of between 150 and 500 RPM. In some versions of the invention, the components internal to the base 32 are selected so that the disc can be rotated at speeds between 250 and 350 RPM. These speeds are understood to be the under-load speeds of the cutting disc 38, when bone stock is pressed against the disc.

Returning to FIG. 2 it can be seen that a spring biased, normally open press button-switch 220 is mounted to the outer top surface of the base foot 46. Switch 220 is mounted to a plate 222. Plate 222 is disposed in a recess 224 in the outer surface of the foot 220. A socket 226 is disposed in an opening in the outer circumferential wall of foot 46. Socket 226 receives the below described that connects the base to the below described control console that actuates bone mill 30. Not illustrated are the circuit board and conductors internal to the base 32 over which conductive connections from the motor flex circuit 122 and switch 220 to the pins internal to the socket 226.

Seen in FIGS. 2 and 4 is the base plate 228 that is disposed over the open bottom end of base foot 46. Not illustrated are the fasteners that hold plate 228 to the foot 46.

III. Mill Head

Figure 11:
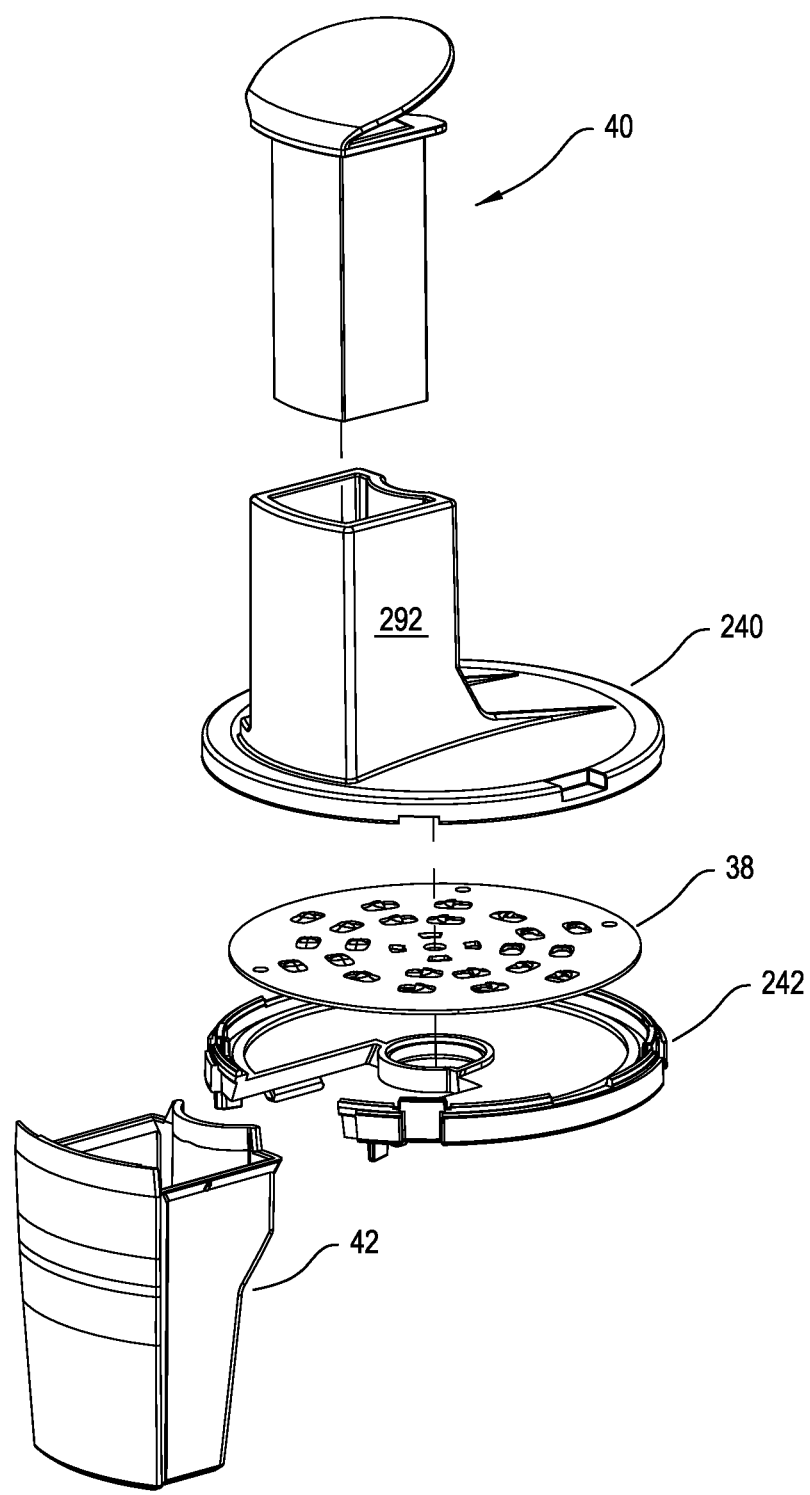
FIG. 11 is an exploded view of the mill head.

The mill head 34, as seen by FIG. 11, includes top and bottom shells 240 and 242, respectively. When assembled together, shells 240 and 242 form the housing of the mill head 34. Cutting disc 38 is disposed between the shells. Mounted to the top shell 240 is an impingement plate 244. The plunger 40 is slidably mounted to the top shell 240 so the bottom surface thereof is directed towards the cutting disc 38. Catch tray 42 is mounted to two parallel rails 358 and 360 (FIG. 15) integral with the bottom shell 242. The catch tray 42 is mounted to the mill head 34 so as to be located below the plunger 40. Owing to the mounting of the catch tray to rails, the tray can be slide radially away from and removed from the rest of the mill head 34.

Figure 12:
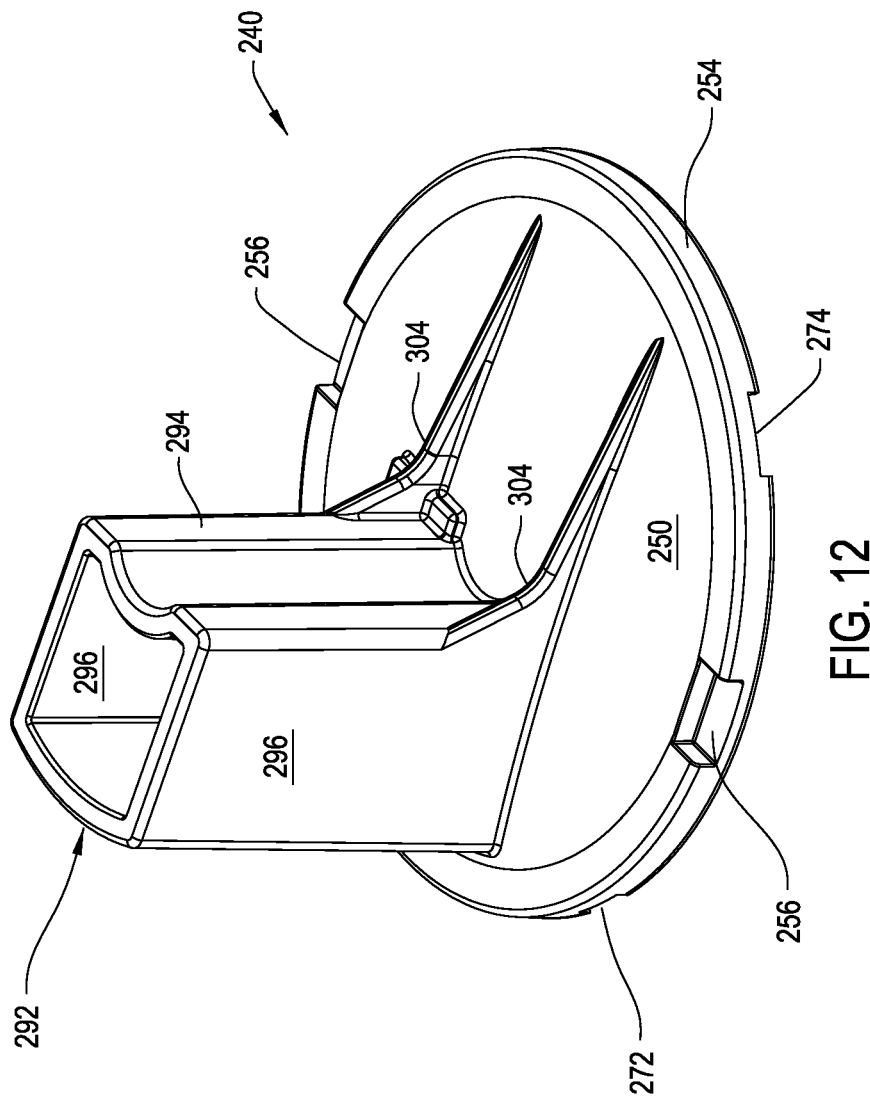
FIG. 12 is a perspective view of the top shell of the mill head housing.
Figure 13:
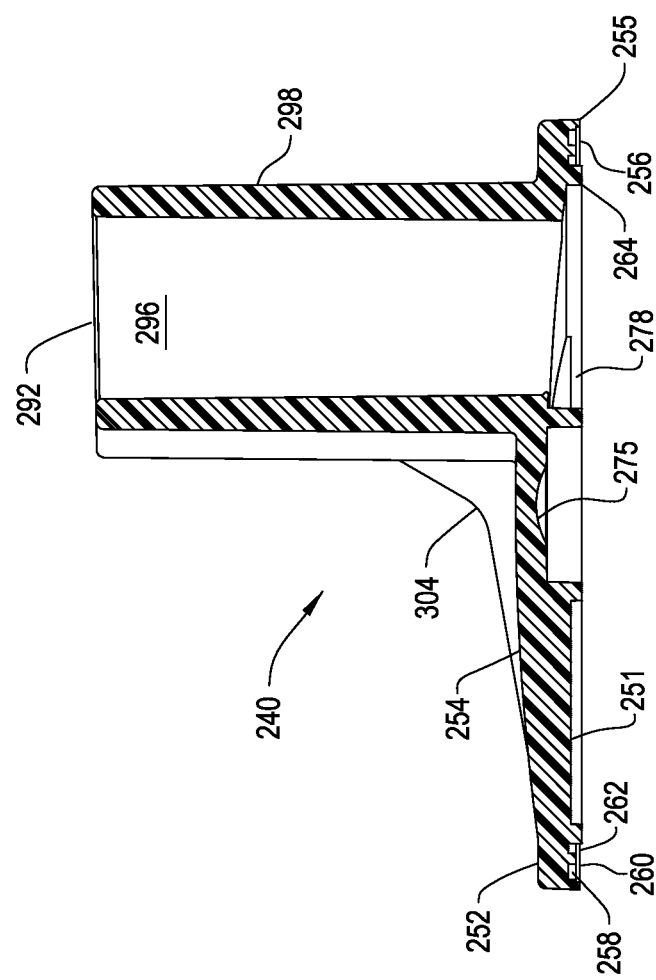
FIG. 13 is a cross sectional view of the top shell.
Figure 14:
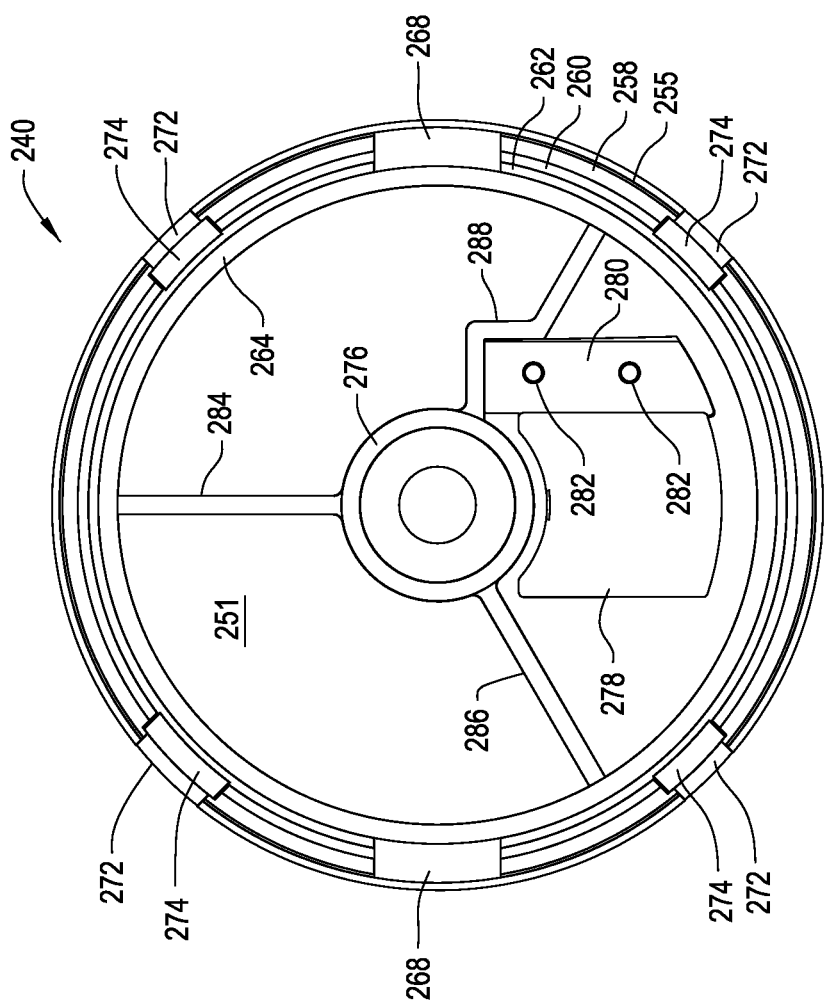
FIG. 14 is bottom plan view of the top shell.

Referring to FIGS. 12, 13 and 14, it can be seen that mill head top shell 240 is formed from a single piece of plastic. One suitable plastic from which top shell is a polycarbonate plastic MAKROLON RX2530 available from Bayer Material Science AG of Leverkusen, Germany. It should be appreciated that the material from which the mill head top shell 240 as well as the other components forming the top shell is formed from, is material that can be successfully subjected to gamma sterilization.

Top shell 240 is shaped to have a circular head 250 that is generally disc shaped. The bottom surface 251 of head 250 can generally be described as planar. The top shell 240 is further formed so that the top surface of the head immediately inward of the perimeter of the head, surface 252, is parallel with the bottom surface of the inward. Inward of this perimeter surface 252, top shell head 250 is formed with a center surface 254 that has a slight rise such that the center of top is located above the outer perimeter surface 252. Top shell head 250 is further formed as to have diametrically imposed indentations 256 each of which intersects perimeter surface 252. Indentations 256 are diametrically opposed from each other. Top shell head 250 is further formed so that each indentation has a side-to-side length that is slightly greater than the width of a base retention arm 88.

An arcuate outer lip 255 extends downwardly from the bottom surface of the top shell head 250. Lip 255 is L-shaped such that inward side of the lip there is a small step 256 that is parallel with the bottom surface of the top shell head 250. Head 250 is further formed so that spaced inwardly from outer lip 255, and concentric with the outer lip 255 there is an inner lip 260. Inner lip 260 has a rectangularly shaped cross sectional profile. Specifically, inner lip 260 extends downwardly so that the bottom surface of lip 260 is coplanar with step 256 integral with the outer lip 255. Between the outer and inner lips 254 and 260, respectively the head 250 defines an annular groove 258. Groove 258 has a base that relative to bottom surface 251 is recessed.

Disposed inwardly of the inner lip 255, top shell head 242 is formed to have a circular outer containment ring 264. Containment ring 264 projects downwardly from the head 250 and has a rectangular cross sectional profile. Between the inner lip 260 and the outer containment ring 264 there is an annular groove 262. The base of groove 262 is in the same plane as that of the surrounding groove 258.

Lips 254 and 260 while curved, are not unbroken circles. Below the sections of outer perimeter surface in which indentations 252 are formed, top shell 232 is molded so that two diametrically opposed rectangular blocks 268 intersect grooves 258 and 262 and inner lip 260. Top shell 240 is further formed so that four equangularly spaced apart gaps 272 separate the outer lip 255 into four sections. Radially aligned with each gap 272 is a slot 274. Each slot 274 separates sections of the inner lip 260 and has a base that extends further into the shell head 250 deeper than the bases of the sections of the grooves 258 and 262 intersected by the slot 274. Each slot 274 subtends an arc greater than that subtended by the adjacent and contiguous outer lip gap 272.

The top shell head 250 is further formed so as to have circular inner containment ring 276 located outwardly of the center of the head. Inner containment ring 276 has a rectangular cross sectional profile. From FIG. 14 it can be seen that the outer and inner containment rings 264 and 276, respectively, define the outer and inner perimeters of the head bottom surface 251. Head 250 is further shaped so that the containment rings 264 and 276 extend downwardly the same distance from bottom surface 251. Also, the surface of the head 250 within the inner containment ring 276 is further from the exposed face of the ring 276 than bottom surface 251. Top shell head 250 is also shaped to define a dome shaped void space 275 that is concentric with the head.

Top shell 240 is further shaped so that there is an opening 278 in head 250. Opening 278 extends from an arcuate edge in the head immediately outward of inner containment ring 276 to an arcuate edge immediately inward of the outer containment ring 264. These arcuate edges are concentric with the center axis of the head 250. Opening 278 is further defined by two parallel side edges in the head 250. Each of the side edges extends between opposed terminal ends of the associated arcuate inner and outer edges.

The top shell head 250 is further formed to define a void space 280 that extends inwardly from bottom surface 251 adjacent opening 278. Void space 280 is formed by an inward step in the material forming the head 250 (step not identified). Void space 280 is positioned to be contiguous with one side of opening 278. More particularly, the void space is adjacent the side of opening 278 towards which the cutting disc 38 rotates when bone mill 30 is actuated. The top shell is further formed to define two mounting posts 282 that extend from head into void space 280. Given the inversion of FIG. 14 relative to the actual orientation of the top disc, it should be understood that posts 282 project downwardly from surface defining the top of the space 280 into the space.

The top shell head 250 also includes three angularly spaced apart reinforcing ribs 284, 286 and 288. Each of the ribs 284-286 extends radially from the inner containment ring 276 to the outer containment ring 264. Each rib 284-286, also projects downwardly from the head bottom surface 251 a distance less than that which the containment rings 264 and 276 downwardly extend. When the mill head 34 is assembled, ribs 284-288 extend over the below-described scallops 378 of the cutting disc 38. Two of the ribs, ribs 284 and 286, are longitudinally centered over radial lines that project from the center of the head 250. The third rib, rib 288, has a number of different sections. There is an inner section that projects from the inner circumferential ring 276 around the inner edge of void space 280. A middle section extends around the forward edge of void space 280, the edge spaced from opening 278. The third section of rib 288 extends from the middle section to the outer containment ring 264. This third section is centered on a radial line that projects from the center of the head 250. The radial lines along which ribs 284 and 286 and the outer section, the third section of rib 288 are centered are equangularly spaced apart from each other.

A hollow feed sleeve 292 also part of top shell 240 extends above head 250 and is disposed around opening 278. In the illustrated versions of the invention, sleeve 292 is a four-walled structure. There is an inner wall 294 adjacent the center of the head 250. Inner wall 294 has three sections. There is a center section that is inwardly curved and two coplanar outer sections (individual sections not identified). There is an outer wall 298 has an arcuate profile. Sleeve 292 has two side parallel side walls 296. Each side wall 296 extends between the outer edge of one of the outer sections of the inner wall 294 and the adjacent outer edge of the outer wall 298. Not identified is the hollow internal to sleeve 292 defined by walls 294-298. This hollow opens into head opening 278. More particularly, top shell head 250 is formed so that opening 278 has a cross sectional profile identical to that defined by the hollow of sleeve 292.

Top shell 240 is also formed with reinforcing members adjacent sleeve 292. In particular, a web 304 flares out from and is coplanar with each side wall. Each web 304 extends over the head center surface 252 on the side of the head opposite the side from which the sleeve 292 projects.

Figure 15:
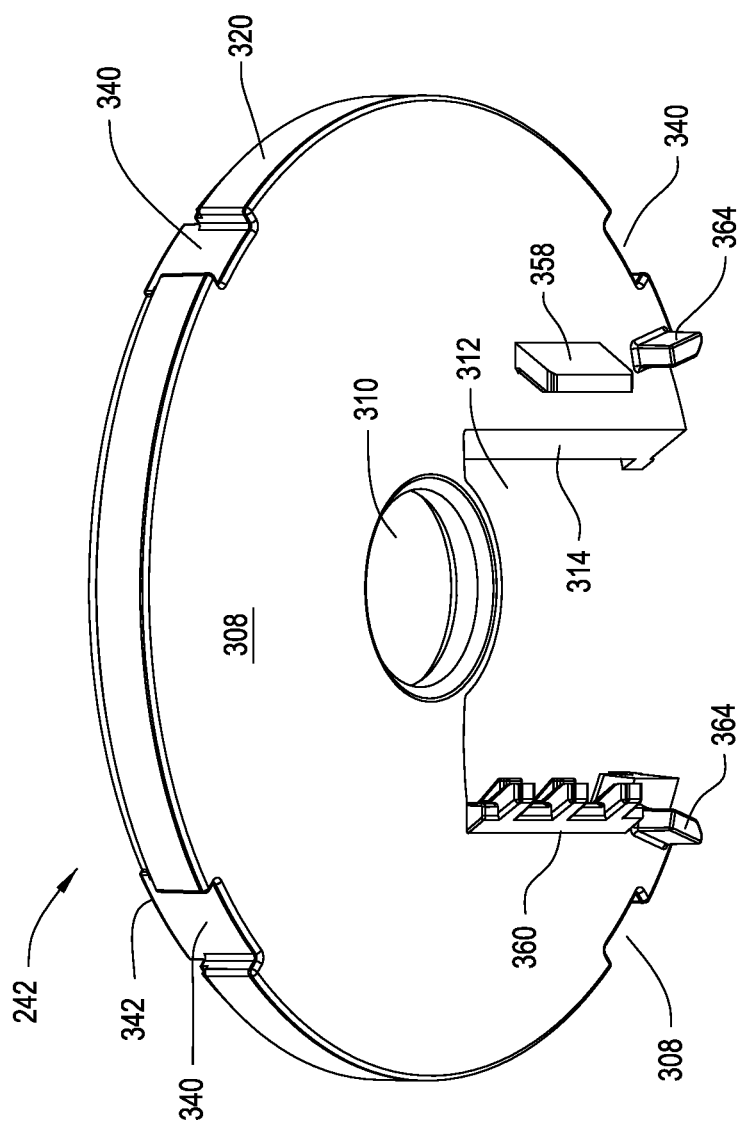
FIG. 15 is a perspective view of the bottom shell and, more particularly, of the exposed bottom surface of the bottom shell.
Figure 16:
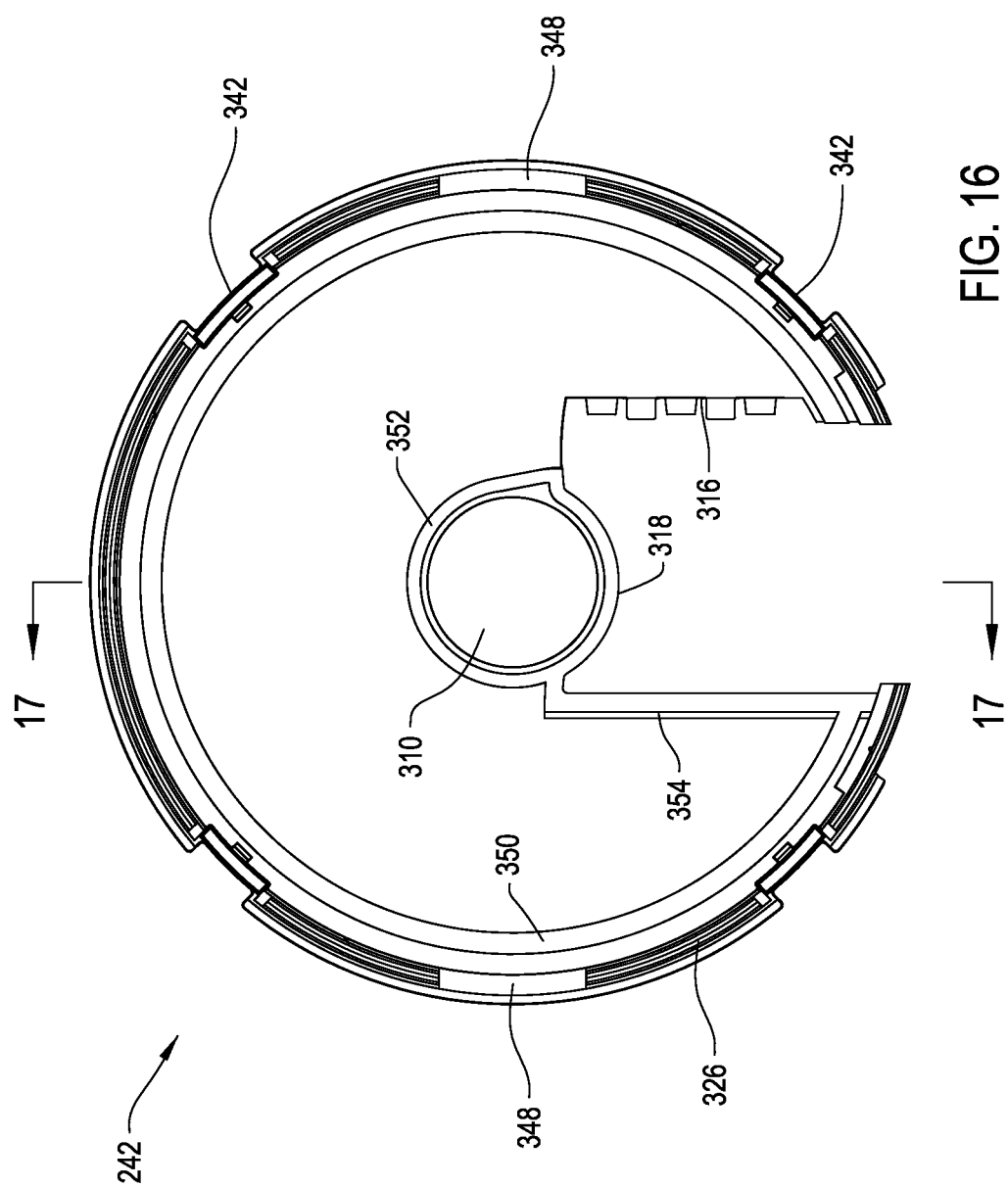
FIG. 16 is a plan view of the interior of the bottom shell.
Figure 17:
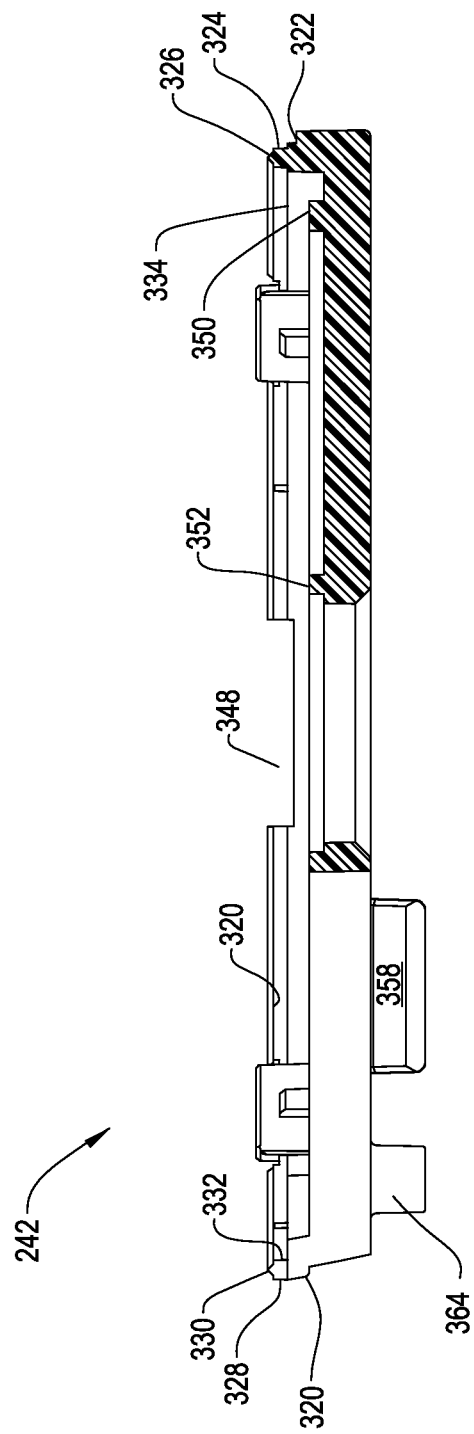
FIG. 17 is a sectional view of the bottom shell taken along line 17-17 of FIG. 16.

Bottom shell 242 of the mill head housing, as seen in FIGS. 15-17, is shaped to have a generally circular shaped body 308. The bottom shell 242 can be formed from the same material from which the top shell 240 is formed. While approximating the shape of disc, shell body 308 is further formed to have through hole 310. Hole 310 is concentric with the longitudinal axis of body 308.

The shell body 308 is further formed to define an opening 312 separate from hole 310. Opening 312 extends inward from body 308 from an arcuate edge in the body located inward of the outer perimeter of the body. Opening 312 is further defined by two parallel interior walls that extend inwardly from the arcuate outer edge. One of the side walls, wall 314 in FIG. 15, is outwardly beveled such that it extending diagonally from the top of opening 312 outwardly to the exposed bottom surface of the shell body 308. Wall 314 also extends upwardly a short distance from the upper inner surface of shell body 308. The side wall opposite wall 314, wall 316 (FIG. 16) extends perpendicular to the planar top face of the shell body 308. The shell body 308 is formed so that walls 314 and 316 extend on either side of the portion of the body that defines holes 310. An inner wall 318 extends between the side walls 314 and 316 to define the inner perimeter of opening 312. Inner wall 318 has a number of different sections, (not identified.) Adjacent each side wall 314 and 316, the inner wall has an outer section that extends perpendicularly inwardly from the adjacent side wall 314 or 316. The inner wall outer section that abuts side wall 314, like side wall 314, is inwardly tapered. Between there outer sections, inner wall 318 has an inwardly curved middle section. The portion of the shell body 308 that defines the middle section of inner wall 318 also defines an adjacent arcuate section of hole 310.

A multi-section lip 320 extends upwardly from the outer perimeter of shell body 308. Lip 320 is formed to define first and second outer steps 322 and 324, respectively. The first outer step 322 is the step located furthest from the center of the shell. Second outer step 324 is located immediately inward of the first outer step 322. Step 324 is located above the inner step. Lip 320 is further formed to define a crown 326 located inwardly of and that extends above the second outer step 324. The crown 326 is formed to have a pyramid-shaped cross-sectional profile so as to define a peak 330. Crown 326 also has outer and inner parallel side surfaces 328 and 332, located on the opposed sides of the peak 330. The side surfaces 328 and 332 thus project upwardly and are perpendicular to the plane of outer step 324. Shell lip 320 is also shaped to have an inner step 334. Inner step 334 is coplanar with the second outer step 324.

Top and bottom shells 240 and 242, respectively, are further formed so that, when assembled, bottom shell crown 326 tightly fits in top shell groove 258. Also the bottom shell first outer step 322 extends over and has an outer diameter generally equal to the most overlying outer most bottom located arcuate surface of top shell outer lip 255. Further the shells 240 and 242 are mutually shaped so that, when assembled together, bottom shell opening 312 subtends the area subtended by top shell opening 278 and the adjacent void space 280.

Four equangularly spaced apart notches 340 are formed in the bottom shell 242. The bottom shell 242 is further formed so that, immediately inward from each notch 340 there is a downwardly extending finger 342. Each finger 342 is shaped to have a curved inner and outer surface, (surfaces not identified). The side-to-side width of each finger 342 is such that the finger can seat in one of the top shell slots 274. Each finger 342 has an inner-to-outer surface depth such that the finger subtends an arcuate section of the bottom shell that would otherwise be subtended by a section of the lip inner step 334 and the adjacent inner surface of the shell body 308. A reinforcing tab 344 is formed integral with each finger 342 so as to extend over the inner surface of the finger. Each tab 344, like the associated finger 342, extends upwardly form the adjacent top located surface of the shell body.

Two of the sections of lip 320 are formed with their own diametrically opposed breaks 348. Each break 348 essentially separates the crown 326 of the associated lip section into two sections. Each break 348 defines an arcuate void space dimensioned so that, when the mill head 34 is assembled, one of the top shell blocks 268 seats in the break.

Located immediately of the circle defined by reinforcing tabs 344, the bottom shell 242 is formed to define a circular outer containment ring 350. Containment ring 350 extends upwardly from the inner surface of the shell body and has a rectangular cross-sectional profile. Bottom shell 242 is further shaped to have an inner containment ring 352. Inner containment ring 352, extends upwardly from the inner surface of the shell body 308 and has an inner diameter slightly greater than that of center hole 310. Like the outer containment ring 350, the inner containment ring has a rectangularly shaped cross-sectional profile. Inner containment ring 352, it should be noted extends over the arcuate section of the shell body 308 that separates hole 310 and opening 312. The outer diameter of the inner containment ring 352 is slightly less than the arc that defines the middle section of the opening 312 defining inner wall 318. In the illustrated version of the invention, for manufacturing reasons, adjacent where the containment ring and side wall 318 the ring is not circular.

Shells 240 and 242 are further constructed so that, when assembled together to form the mill head housing, the top shell containment rings 264 and 276 overlap the bottom shell containment rings 350 and 352, respectively. When the mill head 34 is assembled, shells 240 and 242 are ultrasonically welded together.

A reinforcing rib 354, best seen in FIG. 16, projects away from the inner containment ring 352 of the bottom shell 242. Rib 354 extends over the inner surface of the shell base 308. The rib 354 extends from ring 352 over the portion of the body 308 that defines the section of the inner wall 318 adjacent side wall 314. Owing to its rectangular cross-sectional profile 354, rib 354 is actually flush with the adjacent section of inner wall 318. At the end of inner wall 318, rib bends perpendicularly to extend over the surface of the shell body adjacent the top edge of side wall 314. While rib 354 extends toward the outer perimeter of the shell base the rib terminates a short distance inward of the outer containment ring 350.

Two parallel rails 358 and 360 project downward from the underside of shell base 308. Rails 358 and 360 are the structural members integral with the mill head housing that slidably hold the catch tray 42 to the rest of the mill 34. The rails 358 and 360 are both parallel to opening 312-defining side walls 314 and 316. Rail 358 extends downwardly from the housing body 308 adjacent side wall 314 so as to be spaced away from opening 312. Rail 358 is in the form of a rectangular structure that extends diagonally towards opening 312. Rail 360 extends from the undersurface of the shell body 308 adjacent side wall 316 so as to be spaced from opening 312. Rail 360 is generally in the form of a rectangular structure that extends diagonally toward opening 312. The rails are different in that rail 360 is longer than rail 358. Also, teeth, (not identified) extend from the main body of rail 360. The teeth are present for manufacturing purposes and are otherwise not relevant to this invention. Similar teeth may also project from shell body side wall 316. Again, these teeth are present for manufacturing purposes.

A pair of tabs 364, also project downwardly from the undersurface of shell body 308. Tabs 364 are located between the outer perimeter or the bottom shell 242 and rails 358 and 360. A first one of the tabs 364 is adjacent rail 358 and is oriented to extend away from the longitudinal axis along which rail 358 is centered, away from opening 312. The second tab 364 is adjacent rail 360 and is oriented to extend outwardly relative to opening 312. Tabs 364 are generally in the shape of rectangular blocks. The tabs 364 thus serve as alignment members that facilitate the centering of the catch tray 42 between rails 358 and 360.

Figure 18:
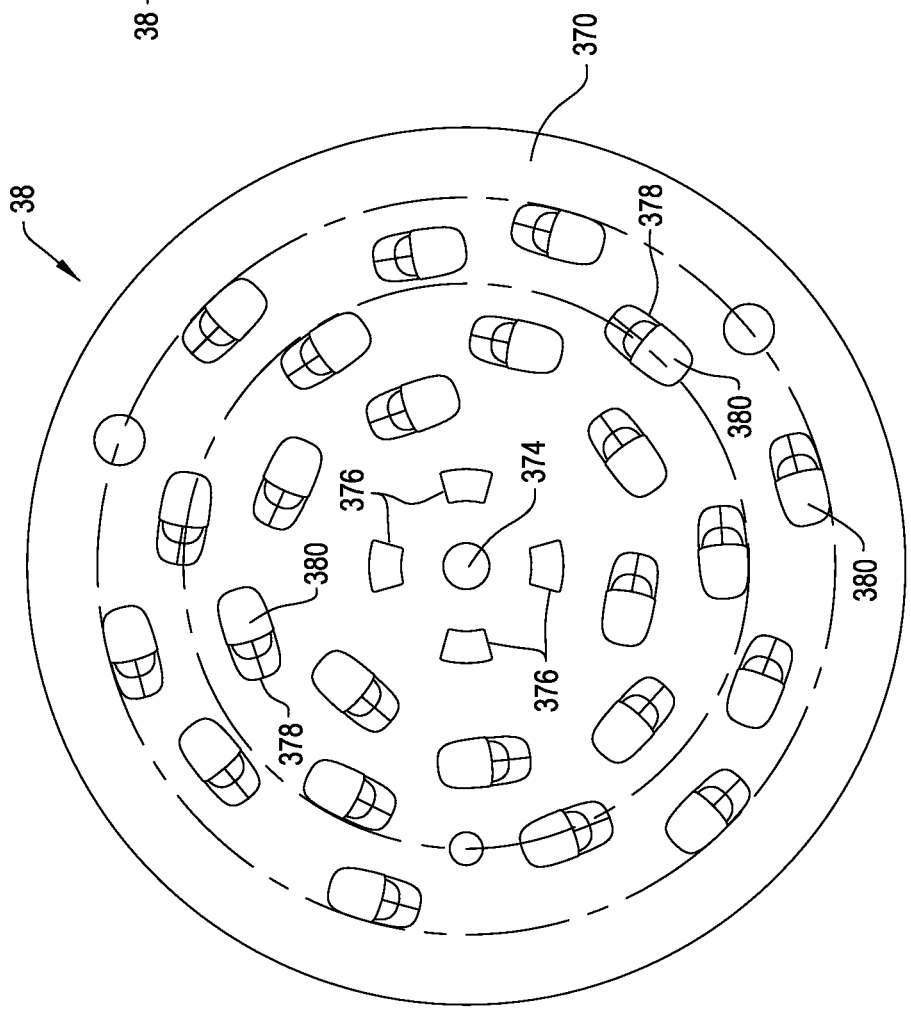
FIG. 18 is a plan view of the cutting disc.

Cutting disc 38, now described with initial reference to FIG. 18, is formed from a material that can be appropriately shaped, that will not fatigue when used to cut bone as described below and that can be subjected to sterilization processes. In some versions of the invention the cutting disc 38 is formed from stainless steel such as 410 Stainless Steel. Generally, the disc 38 has a circular shape with opposed top and bottom surfaces 370 and 372, respectively. The diameter of the cutting disc is approximately 0.10 cm greater than the outer diameter of the outer containment rings 264 and 350 integral with the mill head housing.

The cutting disc 38 is further shaped to have a center-located hole 374. Hole 374 is dimensioned to receive the alignment pin 210 integral with the base spindle 202. Located around hole 374, the cutting disc 38 is formed to have four equangularly shaped apart openings 376. Each opening 376 is shaped to receive a separate one of the teeth 212 integral with spindle 202. Accordingly, openings 376 are arcuately shaped. The circle defined by the outer circumference of openings 376 is less than inner diameter of the inner containment rings 276 and 352 integral with the mill head housing.

Figure 19:
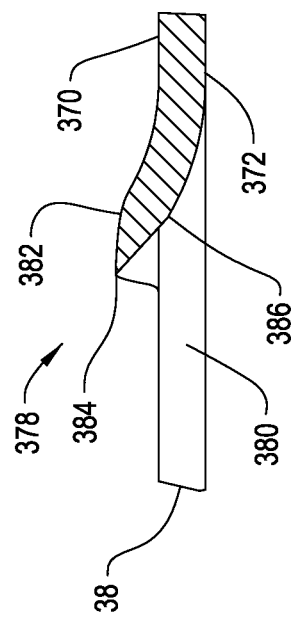
FIG. 19 is a cross sectional view of one of the scallops of the cutting disc.

Cutting disc 38 is further formed to have a number of cutting scallops 378. Integral with and longitudinally axially aligned with each cutting scallop 378, the cutting disc has a through opening 380. As seen in FIG. 19, each scallop 378 is formed by shaping the cutting disc 38 so that the disc top and bottom surfaces 370 and 372, respectively, adjacent the opening 380 curve upwardly into, respectively, a scallop top surface 382 and a scallop bottom surface 386. The scallop top surface 380 is milled so that top surface 382 and bottom surface 386 meet at an edge 384. This edge 384 is the cutting edge of the scallop 378.

Edge 384 is also the edge of the scallop that defines the perimeter of the associated opening 380. Each opening 380 is generally rectangularly shape wherein the long sides extend forward from the scallop 378 with which the opening is integral. Each opening 380 is not exactly in the shape of a rectangular in that the sides of the opening, including the side defined by edge 384 are outwardly bowed. Further, the corners where the sides of the opening 380 meet are rounded.

The cutting disc 38 is formed so that the scallop 378-opening 380 pairs are arcuately and radially spaced apart from each other around the disc. The scallop 378-openings 380 located closest to the center of the disc are radially spaced from the center to lie outside a circle on the disc having a diameter equal to the outer diameter of the inner containment rings 276 and 352. The outermost located scallop 378-opening 380 pairs are located within the circle on the disc that has diameter equal to the inner diameter of the outer containment rings 264 and 350. The scallop 378-opening 380 pairs are further arranged so that no two scallop edges 384 are on the same radial line projecting from the center of the disc 38.

When the mill head 34 is assembled, the cutting disc is sandwiched between the downwardly-directed, top-located containment rings 264, 276 and the upwardly-directed, bottom-located containment rings 350 and 352. Owing to the relative dimensioning of the components, the cutting disc 38 has a top surface 370 to bottom surface 372 thickness that is approximately 0.009 inches (0.23 mm) less than the gap between the aligned containment ring pairs 264-350 and 276-352. Consequently, the cutting disc 38 is able to slightly move, float, in three degrees of freedom within the mill head housing.

Figure 20:
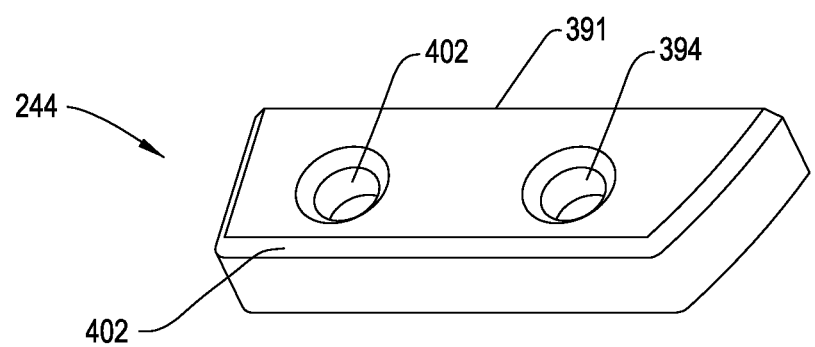
FIG. 20 is a perspective view of the impingement plate.
Figure 21:
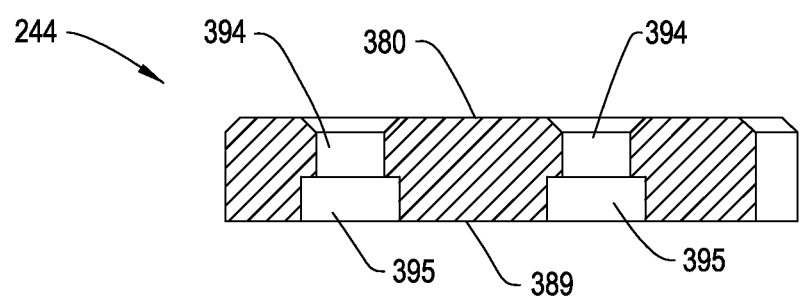
FIG. 21 is a cross sectional view of the impingement plate.

The impingement plate 244, shown in FIGS. 20 and 21, is formed from material that, in addition to being sterilizable, will not fracture when bone is pressed against it. In some versions of the invention, the impingement plate is formed from stainless steel such as 304 stainless steel. The impingement plate 244 is generally in the form of a block that has opposed top and bottom surfaces 388 and 389, respectively. The plate is dimensioned to seat in void space 280 defined within top shell 240. Accordingly, one of the side walls of the impingement plate is curved, (curved side not identified.) Impingement plate has a front face 391 that, in terms of the length is the longer of the two faces of the plate. (In FIG. 20, the edge of front surface 391 is identified.) Impingement plate 244 is further formed so that around the top surface 388 of the plate there is downwardly extending bevel 392.

Two bores 394 extend through the impingement plate from the top surface to the bottom surface. Each bore 394 actually opens from a larger diameter counterbore 395 that extends upwardly from the plate bottom surface 389.

When mill head 34 is assembled, impingement plate 244 seats in top shell void space 280. The impingement plate is positioned so that the front face 391 serves as the surface defining the front of opening 278. Plate top surface 388 abuts the interior of shell 240 that defines the roof of void space 280. When the impingement plate is so positioned, each post 282 seats in a separate one of the bore 394-counterbore 395 pairs. The impingement plate is secured to top shell 240 by heat deforming the tips of the posts 282. The melted plastic form rivets within the counterbores 395.

Figure 23:
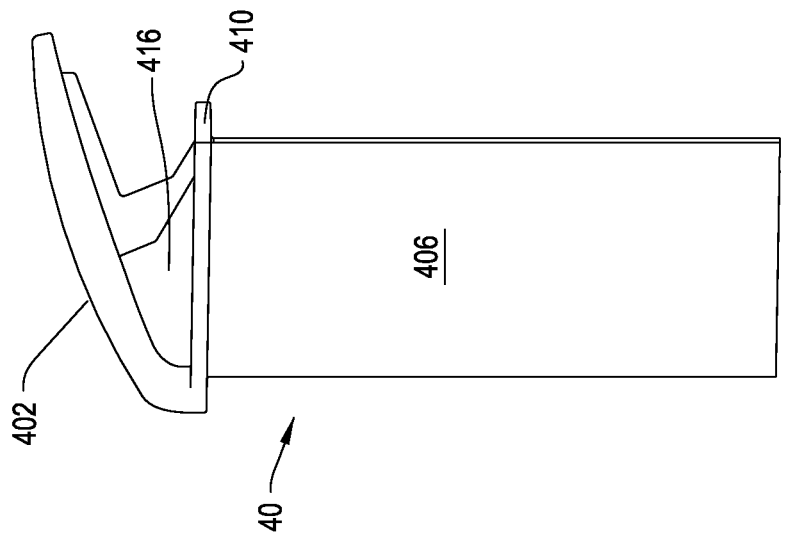
FIG. 23 is a side view of the plunger.
Figure 22:
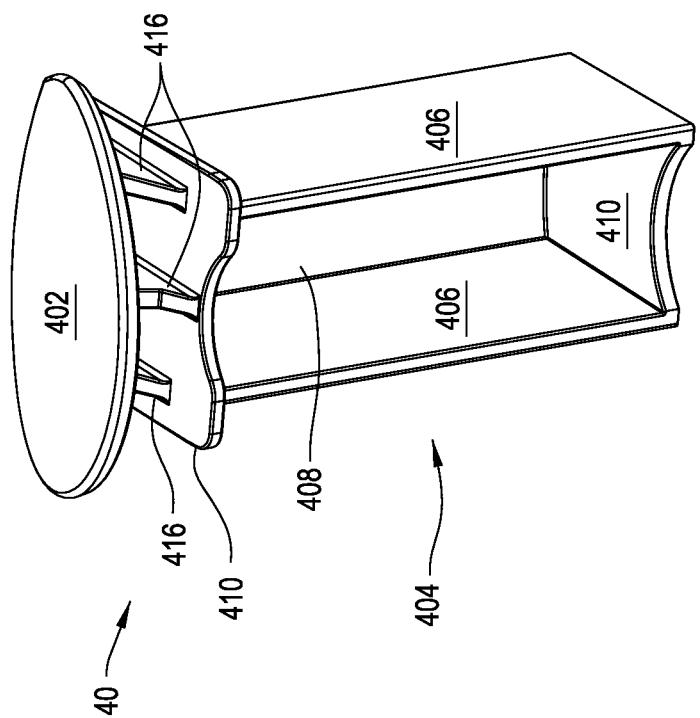
FIG. 22 is perspective view of the plunger.

FIGS. 22 and 23 illustrate plunger 40. The plunger 40 can be formed out of the same material from which the top shell 240 is formed. The plunger 40 is formed to have a head 402 from which a rod 404 extends. Rod 404 is shaped to have two parallel side panels 406 and a front panel 408 that extends between the side panels. A bottom plate 410 extends between the side panels 406 and front panel 408 to form the base or bottom of the rod 404. Rod 404 is dimensioned so that the side panels 406, the front panel 408 and bottom plate 410 can slidably fit in the housing feed sleeve 250. Accordingly, the bottom panel 410 has an exposed edge with an inwardly curved section 412. The curvature of edge section 412 conforms to and is slightly greater than the curvature of the feed sleeve inner wall 294.

Plunger rod 404 also includes a top plate 414. The plunger 40 is formed so that the top plate 414 extends over and projects beyond the side and front panels 406 and 408, respectively. More specifically, the top plate 414 is dimensioned to subtend an area larger than the cross-sectional area of the center void of the housing feed sleeve 250. The top plate 414 thus limits the extent to which the plunger rod 404 can be pushed into the sleeve and the opening 278 immediately below the sleeve. In some versions of the invention, the components of mill head 34 are dimensioned so that when the plunger 40 is completely disposed in sleeve 250 the bottom plate 412 is at least 0.05 cm above the cutting disk 38.

The plunger 40 is further shaped so that head 402 extends diagonally upwardly from the outer perimeter of the rod 404. A number of webs 416 extend between the top of top plate 414 and head 402. Webs 416 provide reinforcing strength to prevent bending of the head 402 relative to the top plate 414.

Figure 24:
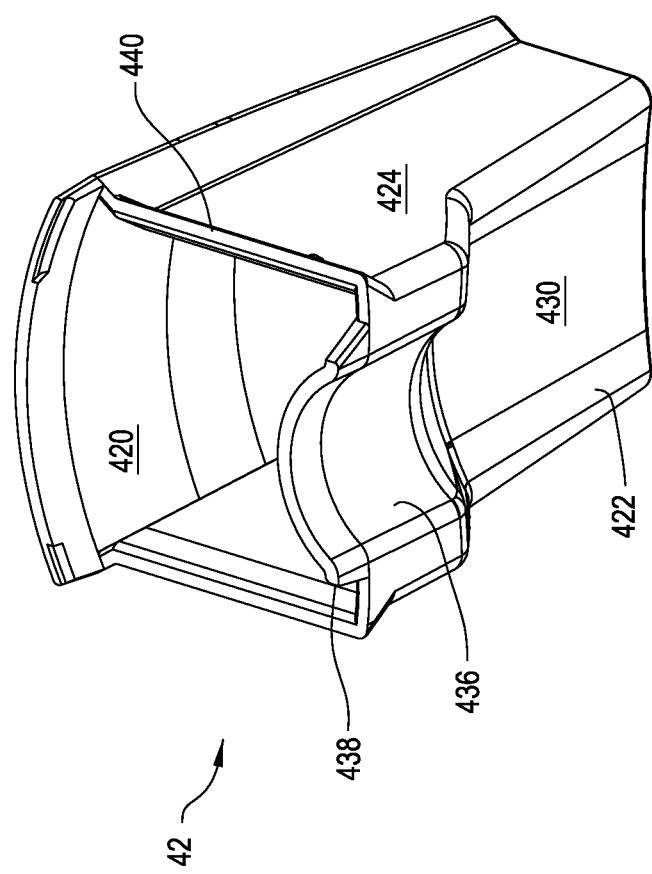
FIG. 24 is a perspective view of the catch tray.
Figure 25:
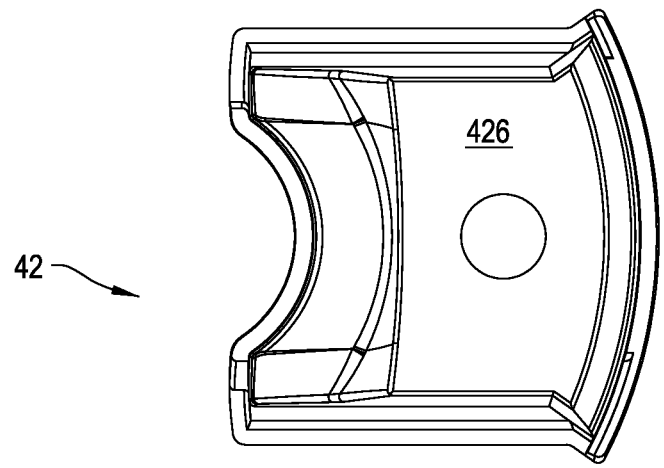
FIG. 25 is a plan view directed towards the interior of the catch tray.
Figure 26:
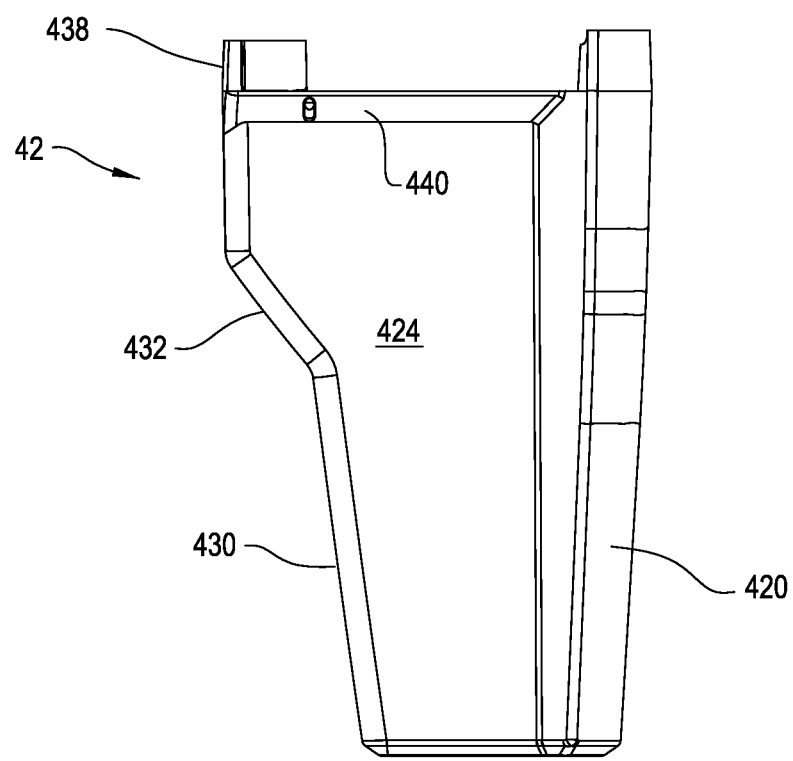
FIG. 26 is a side view of the catch tray.

As seen in FIGS. 24-26, catch tray 42 is formed to have opposed front and rear panels 420 and 422, respectively with side panels 424 located therebetween. A bottom plate 426 extends between the panels at the bottom of the tray 42 to find the base of the tray. In the illustrated version of the invention, front panel 420 has a arcuate profile. For aesthetic reasons, at the top of the panel this profile has a radius of curvature equal to the diameter of top shell 240.

Tray rear panel 422 has a number of different sections. A bottom section 430 extends upwardly from tray bottom plate 426. More particularly, the bottom section extends diagonally upwardly away from plate 426, Panel bottom section 430 is substantially planar. Contiguous with and located above the bottom section 430, rear panel 422 has a top section 432. The top section, like the bottom section extends diagonally away from the bottom plate 426. The outward taper of the panel top section 432 is greater than that of the bottom section 430. Further the catch tray is formed so that there is a circular indentation 436. Indentation 436 has a curvature slightly greater than that of outer perimeter of the arcuate section of the bottom shell body 308 that separates hole 310 from opening 312.

A lip 438 extends upwardly from rear panel top section tray rear panel top section 432. Lip 438, it will further be observed, extends above the tray side panels 424. Lip 438 has the same curvature of indentation 436. Thus, when the tray 40 is mounted to the mill head housing, the outer surface of the lip can abuts the arcuate section of the bottom shell base 308 that defines the inner perimeter of opening 312.

Side panels 424 are parallel planar structures. On each side of the catch tray 40 a separate one of the side panels 424 extends between the opposed side edges of the front panel 420 and the rear panel 424. A flange 440 extends diagonally outwardly from the top edge of each side panel 424. Flanges 440 are dimensioned to seat against the inner surfaces of the bottom shell rails 358 and 360.

IV. Operation

Bone mill assembly 30 of this invention is prepared for use by first attaching mill head 34 to base 32. This is accomplished by placing the base so that the bottom shell 242 seats in the pedestal recess 60. An initial part of this process is the alignment of the mill head so that catch tray 42 is positioned in pedestal notch 70. As a result of this arrangement of components, the longitudinal axis of the mill head 34 is approximately aligned with the longitudinal axis of the base 32. As the mill head bottom shell 242 starts to seat in the pedestal recess 60, the spindle alignment pin 210 extends through shell hole 310. More particularly, the alignment pin 210 extends through the bottom shell hole 310 and enters the cutting disc center hole 374.

Since the cutting disc floats within the mill head housing, the further seating of the mill 34 on the base results in the cutting disc 38 centering itself on the drive spindle alignment pin 210. As the mill head 34 is further seated against the base 32, the spindle teeth 212 may or may not be aligned with, be seated in, the complementary openings 376 formed in the disc 36. In either situation, the movement of the cutting disc 36 against the spindle 202 overcomes the force spring 216 places on the spindle to urge the spring upwardly. Thus, the seating of the mill head 34 in the base recess 60 results in at least some retraction of the spindle 202 toward the base foot 46. The maximum retraction occurs in instances in which the spindle teeth 212 are not seated in the disc openings 376.

As part of the fitting of the mill head 34 on the pedestal, pedestal teeth 80 seat in bottom shell notches 340. As a consequence of the fitting of the mill head catch tray 42 in the pedestal notch 70, the pedestal teeth 80 are inherently aligned with the complementary bone bottom shell notches 340. Further, as a result of this seating of the mill head 34 in the pedestal recess 60, each indentation 252 in the mill head top shell 240 is positioned adjacent a separate one of the restraining arms 88.

The mill head 34 is then secured to the base by pivoting the retention arms 88 upwardly. This displacement of a retention arm results in the tip of the arm finger 98 seating in the adjacent indentation 252 in the mill head top shell 240. Spring 112 holds the arm 88 in this position.

As part of the process of preparing the bone mill for use, the base 32 is connected to a complementary console that provides signals for energizing the motor 36. One such console is sold by the Stryker Corporation of Kalamazoo, Mich. as the CORE™ Console. A description of the circuitry internal to this console that can be used to power motor 36 is presented in U.S. Pat. Pub. No. US 2006/0074405 A1, the contents of which is incorporated herein by reference. A cable (not illustrated) extends from base socket 226 to a complementary socket integral with the associated console. Conductors over this cable provide the on/off signal to the console; selectively apply enegization signals to the windings internal to the motor; and provide the signals from the sensors internal to the motor back to the control console. The above-mentioned CORE Console is capable of actuating surgical instruments other than bone mill 30 of this invention. In other versions of the invention, a console specifically designed to energize motor 36 may be provided. Accordingly, the exact structure of the console used to supply the energization signals to the motor 36 is not relevant to this invention.

Bone, either allograft or autograft in nature, is loaded in the mill head feed sleeve 292. Once the bone is so loaded, the plunger 40 is disposed in the feed sleeve.

The bone chips are produced by simultaneously actuating the cutting disc 38 while the plunger 40 is depressed to force the bone against the disc. Cutting disc 38 is actuated by depressing switch 220 so as to cause the actuation of the base motor 36. The actuation of the motor results in the rotation of spindle 202.

As mentioned above, when the mill head is fitted to the base, the spindle teeth 212 may already be engaged in the disc openings 376. In this situation, the rotation of spindle 202 results in the immediate like rotation of the cutting disc 38. There is, however, the potential that initially the cutting disc 38 and spindle 202 are not so aligned. In this event, the initial rotation of the spindle results in the spindle teeth 212 engaging in an arcuate path of travel against the disc bottom surface 312. Teeth 212 so move against the disc until the teeth come into registration with the disc openings 376. When this event occurs, spring 216, which exerts an upward force on the spindle 202, pushes the spindle upward so that the teeth 212 seat in the disc openings 376. Once this event occurs, the cutting disc 38 rotates in unison with the spindle 202.

The rotation of the cutting disc 38 means that the disc scallops 378 are rotated towards the impingement plate 244. More particularly, owing to the assembly of the mill head 34, the scallops 378 are rotated so as they pass under top shell opening 278, scallop edges 380 rotate towards the impingement plate 244. As mentioned above, simultaneously with the rotation of the cutting disc 38, the plunger 40 pushes the basic bone stock through opening 278 against the cutting disc 38. As disc 38 rotates, the lower portion of the bone stock is wedged between the scallop edges 384 and the impingement plate front face 391. The continued rotation of the cutting disc causes the disc edges 384 to shear the bone wedged between the disc scallops and the impingement plate away from the bone stock. A sheared bone chip enters the cutting disc 380 opening defined by the disc edge that sheared the chip from the stock. From the disc opening 380, the chip falls through the bottom shell opening 312 into catch tray 42.

During the chip formation process, some chips may initially adhere to the disc bottom surface. These chips abut bottom shell wall 314. Wall 314 thus serves as a wiper that prevents the bone chips from rotating with the disc 38. The chips, if they adhere, remain in the area above bottom shell opening 312. Also during the chip formation process, inner containment ring 352 integral with bottom shell 242 functions as a barrier that prevents the chips from being discharged through opening 310. Inner containment ring 276 integral with top shell 240 serves as barrier that prevents lose material integral with the bone stock from migrating towards the center of the cutting disc 38 where the material could exit through openings 374 and 376.

In the described version of the invention, the reduction in speed of the rotational motion of the motor shaft by gear train 134 significantly increases the torque at stall the available from the drive spindle 202. Specifically, in some versions of the invention, the gear train reduces the speed of the spindle down to between 250 and 300 RPM. At a speed within this range and using the described motor, the spindle is able to output at least 75 inch/pounds of torque and usually 100 inch/pounds or more of torque. Since the spindle is able to provide this relatively high quantity of torque, the likelihood that, when a piece of bone stock is pressed against the cutting disc 38, motor 36 will stall is substantially eliminated.

Owing to the relative dimensioning of the mill 34 components, the plunger top plate 414 functions as a stop that prevents the bottom of the plunger rod 404 from being pressed against the cutting disc 38.

Once a sufficient volume of bone chips have been formed the motor 36 is stopped. Catch tray 42, with the bone chips contained therein, is removed from the mill head 34. As a result of the process of sliding the catch tray 42 away from the mill head housing, tray lip 438 sweeps below the section of the disc bottom surface 372 disposed immediately above bottom shell opening 312. Lip 438 catches bone chips that may be adhering to this section of the cutting disc 38 and the underside of the wiper rib 314. The bone chips are retrieved from the catch tray 42 for use.

The mill head 34 of this invention is provided with a planar cutting disc 38. Owing to disc 38 having this geometry it can be more economical to provide than other cutting blades such as a cylindrical or bent angle blade. The cost minimization associated with this component helps make it possible to provide the mill head 34 as a pre-sterilized, use once-and-dispose component. Thus, between uses of bone mill 30, medical personnel do not have to concern themselves with sterilizing the cutting disc 38, with all its sharp edges 384.

As discussed above, bone mill 30 of this invention is further constructed so that the seating of the mill head 34 on the base 32 results in the alignment of the floating cutting disc 32 with the drive spindle 202. The need to provide a means to precisely hold the cutting disc in a fixed position and so that it can rotate around that position is eliminated. The elimination of the cost associated with providing this sub-assembly further contributes to the economics that make it possible to provide mill head 34 as a use-once disposable.

Cost minimization is further achieved by the fact that holes 376 serve as the features that couple the cutting disc 38 to the drive fasteners. The need to provide supplemental fasteners to perform this function is eliminated.

Bone mill 30 of this invention is further constructed, so that as soon as most chips are cut, they are ejected through the opening 380 associated with scallop 378 that cut the bone. From opening 380, the chips typically falls into catch tray 42. Thus, substantially all the bone chips formed in the mill head 34 are subjected to a single cut, a single pass against either the cutting disc 38 or impingement plate 244. Since the bone chips are only subjected to a single pass against these components, the amount of frictional heating to which the bone chips are exposed as a result of such contact is likewise held to a minimum. This reduction in chip heating results in a like minimization of the extent to which such heating damages the material forming the chips.

Another benefit gained by the design feature that each chip is only pressed against the cutting disc 38 or impingement block 244 once is that the chip is not reduced to below the desired size. Further, few chips, when cut may adhere to the disc bottom surface 372. Substantially all the chips, immediately on formation, are forced into the catch tray 42. Thus, the chips formed with mil 30 are generally of the same size, Base 32 and mill head 34 of the assembly 30 of this invention are further constructed so that as consequence of the pedestal teeth 70 seating in mill indentations 252, the teeth inhibit the transfer of the rotational moment of the cutting disc 38 to the rest of the mill 34. The rotational blocking effect of these teeth 70 minimizes the extent to which the restraining arms 88 have to likewise perform this function. This rotation-stopping effect of the teeth serves to minimize the side and/or number restraining arms. Thus in most versions of the invention, a maximum of two restraining arms or other fastening members are required to releasable hold the mill 34 to the bone 32.

Once a mill head of this invention is used, the catch tray 42 is reattached from the mill head housing. Mill head 34 is disconnected from base 32 by pivoting the restraining arms 88 away from the mill top shell 240. The biasing force of spring 216 displaces the mill a slight distance above the base pedestal 50. Thus, spring 216 facilitates the separation from of the mill head 34 from the base 32. Moreover, post use, the openings 278 and 312 in the mill housing that expose the cutting disc 38 are covered by, respectively, the plunger 40 and the catch tray 42. This reduces the likelihood that persons handling the mill 34 post use, could inadvertently come into contact with the biological material and sharp disc edges 384 inside the housing. Also, given the presence of the sleeve 296 over opening 278 and the relatively small size of opening 312, even if the plunger and catch tray are removed, it is unlikely fingers can come into contact with the disc 38.

Still another feature of bone mill 30 of this invention is that by changing the mill head 34, the mill can be used to provide chips of different sizes. More particularly, individual mill heads can be provided with cutting discs 38 that have different sized openings. Here opening "size" is defined by the width across the opening below the cutting edge 384. In one version of the invention, this width may be 8 mm across. Mill heads with this size disc openings are used to form large sized, coarse sized, bone chips. A mill head 34 with a disc 38 having openings 380 with widths of 5 mm across is used to form medium sized bone chips. Alternatively, one could use a mill head 34 with a cutting disc 38 that has openings with a width of 3 mm across. This particular type of mill head is used to form fine sized bone chips.

V. Alternative Embodiments

The above is limited to one specific version of the bone mill of this invention. Alternative versions are possible. For example, there is no requirement that all versions of the invention include each of the above-described features.

Alternative versions of the described features are also possible. Thus, there is no requirement that in all versions of the invention, the cutting device be the above-described circularly shaped disc. In some versions of the invention, the cutting device may be a blade like device. such a device may include a number of blade like arms that project outwardly from a center hub.

Also, while the above-described embodiment of the mill head of this invention has a use-once disposable mill head 34, other versions may be designed that have more sterilizable and reusable components. Thus, in one alternative version of this invention, the mill head has a bottom section that is integral from the base. The mill head includes a removable top. After use of this version of the invention, the mill top is removed. This allows access to the cutting device for either sterilization or replacement. Separation of the two sections of the mill also makes it possible to access the interior portions of the mill for cleaning.

In some versions of the invention, the complementary geometric features that facilitate the alignment of the cutting device with the drive spindle that rotates the cutting device may be different from what is described above. Thus in some versions of the invention, an alignment pin may project away from the cutting device. In these versions of the invention, the drive spindle is formed with a bore positioned to receive the pin. The bore may be conical in profile such that as the pin enters the bore the pin as well as the whole of the cutting device, is centered relative the drive spindle.

Likewise, the configuration of the of the complementary coupling features on the cutting device and drive spindle that transfer torque to the cutting device may vary from what has been described. In some versions of the invention, teeth may project from the cutting device. These teeth engage in complementary slots or openings associated with the drive spindle.

The structure of the fixed features of the base 32 and removable mill 34 that inhibit rotation of the base are also not limited to what has been disclosed. For example, small fingers may protrude from the mill. In these versions of the invention, the base 32 is provided with slots for receiving the fingers. In some versions of the invention the anti-rotation pin that prevents rotation of the gear train housing 136 may be a pin that extends into a bore that extends radially into the housing. In some versions of the invention, either one or both of the plunger 40 and catch tray 42 have structural features that prevent their unintended removal from the rest of the mill head 34. These features may be detents or notches for receiving detents. If the feature is a detent, this member seats in a slot formed in the head 34. If the feature is a notch for receiving a detent, the detent is a static component located at a complementary location elsewhere on the head.

Alternative assemblies for releasably securing the mill head 34 to the base 32 may likewise be provided. One such assembly may include a set of restraining arms that move in a horizontal plane to engage and release from the mill head. In some versions of the invention, the release arms are attached to the mill head.

Likewise, some versions of the invention may have different assemblies for releasably holding the mill head 34 to the base 32 and blocking the mill from rotation. For example, in one alternative version of the invention one of the base or mill is provided with L-shaped tabs. The other of the mill or base is provided with key-hole type slots for receiving the tabs. Once the mill is seated and rotated, the engagement of the tabs in the slots prevent mill removal. In these versions of the invention, retractable teeth integral with the base may be extended to seat in slots formed in the mill. These teeth inhibit mill rotation.

Alternative structures of the cutting disc are also possible. While typically not useful, a disc could have just a single opening-defining cutting edge. A disc with one or just a few openings may be desirable for certain slow precision processes for forming bone chips. Further, in some versions of the invention, the disc may be formed so that the opening-defining edge against which the bone impinges and that forces its separation from the bone stock is not located above the disc top surface.

In some embodiments of the invention, a hand crank is attached to the mill head. This hand crank is connected to the cutting device to rotate the cutting device. An advantage of this version of the invention is that it eliminates the need to provide the motor. In some versions of this embodiment of the invention a gear assembly connects the hand crank to the motor. This arrangement allows the user to with one hand, push the plunger downwardly so that the bone is pressed against the cutting device while the other hand is used to turn the crank.

Therefore, it is the goal of the appended claims to cover all such modifications and variations that come within the rue spirit and scope of this invention.

What is claimed is:

1. A mill head for use with a bone mill, said mill head including:
   a shell, said shell having: opposed and spaced apart top and bottom sections; a centrally located longitudinal axis that extends top-to-bottom through said shell; a first opening in the shell top section; a second opening in the shell bottom section; and a third opening in the shell bottom section, the third opening being closer to the longitudinal axis of the shell than the second opening;
   an impingement surface integral with the top section of said shell;
   a cutting device movably disposed in said shell between the impingement surface and shell bottom section, said cutting device including: at least one cutting feature located between the shell first and second openings, said cutting feature configured to press bone stock introduced into the shell first opening against the impingement surface so that the bone stock is converted to bone chips that are discharged through the shell second opening;
   a coupling feature integral with said cutting device that is accessible through the shell third opening, said coupling feature configured to engage a spindle of the bone mill so that the rotation of the spindle results in the like rotation of the said cutting device; and
   a first ring that extends upwardly from an inner surface of the shell bottom section around the third opening so as to separate the second and third openings and prevent the discharge of bone chips through the third opening.

2. The mill head of claim 1, wherein said impingement surface is part of an impingement plate that is separate from the shell top section and that is attached to the shell top section.

3. The mill head of claim 1, wherein said cutting device is formed with at least one opening that is accessible through the shell third opening, said cutting device at least one opening being said coupling feature integral with said cutting device.

4. The mill head of claim 1, wherein:
   said cutting device is mounted in said shell to both rotate in said shell and to at least one of move along either the axis of rotation or move along or around another axis; and
   an alignment feature is attached to said cutting device for engaging a complementary alignment feature associated with the spindle so that the engagement of the alignment features positions said cutting device relative to the spindle so that the spindle can engage said coupling feature.

5. The mill head of claim 4, wherein said coupling feature attached to said cutting device and said alignment feature attached to said cutting device are different features.

6. The mill head of claim 1, wherein a catch tray is removably attached to said shell so as to be located below the shell second opening.

7. The mill head of claim 1, wherein:
said cutting device is formed to have: a top surface that is directed to the shell top section; a bottom surface that is directed to the shell bottom section; and a thickness between the top and bottom surfaces;
there is a vertical gap in said shell between said first ring and an opposed adjacent surface of the shell top section, the gap having a distance thereacross;
said cutting device is disposed in said shell so as to be seated on said first ring; and
the thickness of said cutting device is less than the distance across the gap in said shell.

8. A mill head for use with a bone mill, said mill head including:
a shell, said shell having: opposed and spaced apart top and bottom sections; a centrally located longitudinal axis that extends top-to-bottom through said shell; a first opening in the shell top section; a second opening in the shell bottom section; and a third opening in the shell bottom section, the third opening being closer to the longitudinal axis of the shell than the second opening;
a first ring that extends downwardly from the shell top section so as to extend around the shell third opening;
a cutting device movably disposed in said shell between the shell top shell top section and the shell bottom section, said cutting device including at least one cutting feature located radially outwardly of the first ring and between the shell first and second openings that is configured to convert bone stock introduced into the shell first opening into bone chips that are discharged through the shell second opening;
a coupling feature integral with said cutting device that is accessible through the shell third opening, said coupling feature configured to engage a spindle of the bone mill so that the rotation of the spindle results in the like rotation of the said cutting device; and
a second ring that extends upwardly from an inner surface of the shell bottom section around the third opening so as to separate the second and third openings and prevent the discharge of bone chips through the third opening.

9. The mill head of claim 8, wherein
a third ring extends upwardly from the shell bottom section, said third ring being spaced away and located radially outwardly from the second ring;
said cutting device is dimensioned to seat over said second ring and said third ring; and
said at least one cutting feature is disposed on said cutting device to be located between said second ring and said third ring.

10. The mill head of claim 8, wherein:
the shell top section has an impingent surface; and
said cutting device at least one cutting feature is configured to press bone stock against the shell top section impingement surface so as to cause the shearing of bone stock against the impingement surface into bone chips.

11. The mill head of claim 8, wherein:
said cutting device is mounted in said shell to both rotate in said shell and to at least one of move along either the axis of rotation or move along or around another axis; and
an alignment feature is attached to said cutting device for engaging a complementary alignment feature associated with the spindle so that the engagement of the alignment features positions said cutting device relative to the spindle so that the spindle can engage said coupling feature.

12. The mill head of claim 11, wherein said coupling feature attached to said cutting device and said alignment feature attached to said cutting device are different features.

13. The mill head of claim 8, wherein:
in said shell between said first ring and said second ring there is a gap between said rings, the gap having a vertical distance; and
said cutting device has: a top surface located adjacent said first ring; a bottom surface located adjacent said second ring; and a thickness between the top and bottom surfaces, the thickness being less than the vertical distance of the gap between said rings.

14. The mill head of claim 8, wherein said shell is further formed so that said first ring at least partially overlaps said second ring.

15. The mill head of claim 8, wherein a catch tray is removably attached to said shell so as to be located below the shell second opening.

16. A mill head for use with a bone mill, said mill head including:
a shell, said shell having: opposed and spaced apart top and bottom sections; a centrally located longitudinal axis that extends top-to-bottom through said shell; a first opening in the shell top section; a second opening in the shell bottom section; and a third opening in the shell bottom section, the third opening being closer to the longitudinal axis of the shell than the second opening;
a first ring that extends upwardly from the shell bottom section and that is located around the shell third opening so as to be between the shell second and third openings;
a second ring that extends upwardly from the shell bottom section that, relative to the longitudinal axis of the shell, is located radially outwardly and is spaced away from said first ring;
a cutting device movably disposed in said shell between the shell top shell top section and the shell bottom section, said cutting device being dimensioned to seat over said first ring and said second ring, said cutting device including: at least one cutting feature located radially outwardly of the first ring and radially inwardly of said second ring, said at least one cutting feature configured to convert bone stock introduced into the shell first opening into bone chips that are discharged through the shell second opening; and
a coupling feature integral with said cutting device that is accessible through the shell third opening, said coupling feature configured to engage a spindle of the bone mill so that the rotation of the spindle results in the like rotation of the said cutting device.

17. The mill head of claim 16, wherein:
said cutting device is a disc; and
a plurality of said cutting features are formed on said disc.

18. The mill head of claim 16, wherein
the shell top section has an impingement surface;
said cutting device is a disc that has opposed top and bottom surfaces and is positioned so that the top surface is located adjacent the shell impingement surface and the bottom surface is located adjacent said first and second rings; and
said at least one cutting feature includes a scallop that extends up from the top surface of said disc towards the shell impingement surface and said disc is further formed so that said scallop at least partially defines an opening in said disc.

19. The mill head of claim 16, wherein:
said shell has a space in which said cutting device is disposed and said shell has a surface that defines an outer perimeter of the space in which said cutting device is seated; and
said second ring is located radially inwardly and spaced away from the shell surface that defines the outer perimeter of the space in which said cutting device is seated.

20. The mill head of claim 16, wherein:
in said shell there is a vertical gap having a distance between said first and second rings and an opposed spaced apart surface of the shell top section; and
said cutting device has a top surface has: a top surface that is directed towards the shell top section; a bottom surface that is directed towards said first ring and said second ring; and a thickness between the top and bottom surfaces, the thickness being less than distance of the vertical gap in said shell between said first and second rings and the opposed spaced apart surface of the shell top section.

21. The mill head of claim 16, wherein the shell bottom section is formed so that the shell second opening interrupts said second ring.

22. The mill head of claim 16, wherein a catch tray is removably attached to said shell so as to be located below the shell second opening.

23. The mill head of claim 16, wherein:
said second ring has an outer diameter; and
said cutting device is formed to have a length thereacross that is greater than the outer diameter of said second ring.

24. A mill head for use with a bone mill, said mill head including:
a shell, said shell having: opposed and spaced apart top and bottom sections; a centrally located longitudinal axis that extends top-to-bottom through said shell; a first opening in the shell top section; a second opening in the shell bottom section; and a third opening in the shell bottom section, the third opening being closer to the longitudinal axis of the shell than the second opening;
an impingement surface integral with the top section of said shell;
a cutting device movably disposed in said shell between the impingement surface and shell bottom section, said cutting device including: at least one cutting feature located between the shell first and second openings configured to press bone stock introduced into the shell first opening against the impingement surface so that the bone stock is converted to bone chips are discharged through the shell second opening;
a first ring that extends downwardly from an inner surface of the shell top section that is directed towards said cutting device so as to limit movement of said cutting device towards the shell top section and the impingement surface; and
a coupling feature integral with said cutting device that is accessible through the shell third opening, said coupling feature configured to engage a spindle of the bone mill so that the rotation of the spindle results in the like rotation of the said cutting device.

25. The mill head of claim 24, wherein:
said cutting device is configured to rotate around an axis that extends through the third opening of said shell and said at least one cutting feature is located radially outwardly of the third opening of said shell; and
said first ring extends over said cutting device so as to be located radially inwardly of the at least one cutting feature.

26. The mill head of claim 24, wherein:
said shell is formed so that there is a gap between said first ring and an underlying surface of the bottom section of said shell, the gap having a distance; and
said cutting device has a thickness less that the distance of the gap in said shell so that said cutting device can, within said shell, move between said first ring and the underlying surface of the bottom section of said shell.

27. The mill head of claim 24, wherein:
said cutting device has a top surface that is directed towards the inner surface of the top section of said shell; and
said cutting device is formed so that said at least one cutting feature extends above the top surface of said cutting device; and
said first ring extends downwardly from the inner surface of the top section of said shell to hold said at least one cutting feature of said cutting device under the impingement surface.

28. The mill head of claim 24, wherein said impingement surface is part of an impingement plate that is separate from the shell top section and that is attached to the shell top section.

29. The mill head of claim 24, wherein said cutting device is formed with at least one opening that is accessible through the shell third opening, said cutting device at least one opening being said coupling feature integral with said cutting device.

30. The mill head of claim 24, wherein a catch tray is removably attached to said shell so as to be located below the shell second opening.

31. The mill head of claim 24, wherein a barrier is disposed in said shell between the second opening and the third opening to prevent the discharge of bone chips through the third opening.

32. The mill head of claim 31, wherein said barrier is a second ring that extends upwardly from an inner surface of the bottom section of the shell towards the top section of said shell.

33. The mill head of claim 24, wherein:
said cutting device is a disc; and
a plurality of said cutting features are formed on said disc.

34. The mill head of claim 24, wherein:
said cutting device is mounted in said shell to both rotate in said shell and to at least one of move along either the axis of rotation or move along or around another axis;
an alignment feature separate from said cutting feature is attached to said cutting device for engage a complementary alignment feature associated with the spindle so that the engagement of the alignment features positions said cutting device relative to the spindle so that the spindle can engage said coupling feature.

35. The mill head of claim 24, wherein:
said cutting device is configured to rotate around an axis that extends through the third opening of said shell and said at least one cutting feature is located radially outwardly of the third opening of said shell;

said first ring extends over said cutting device so as to be located radially inwardly of the at least one cutting feature; and at least one rib extends downwardly from the inner surface of the shell top section and outwardly from said first ring so as to extend over the at least one cutting feature of said cutting device.

36. The mill head of claim 35, wherein a plurality of said ribs extend outwardly from said first ring.

37. The mill head of claim 35, wherein said shell is formed so that said at least one rib extends downwardly from the inner surface of the shell top section a distance less than the a distance said first ring extends downwardly from the inner surface of said shell top section.

38. The mill head of claim 35, wherein said at least one rib extends linearly outwardly from said first ring.

39. The mill head of claim 35, wherein:

said shell is further formed to have a second ring that extends downwardly from the inner surface of shell top section and that is located outwardly of said first ring and so that said at least one cutting feature of said cutting device is located between said first and second rings; and said at least one rib extends from said first ring towards said second ring.

40. The mill head of claim 35, wherein:

said shell is further formed to have a second ring that extends downwardly from the inner surface of shell top section and that is located outwardly of said first ring and so that said at least one cutting feature of said cutting device is located between said first and second rings; and said at least one rib extends from said first ring to said second ring.

41. The mill head of claim 24, wherein:

said cutting device is configured to rotate around an axis that extends through the third opening of said shell and said at least one cutting feature is located radially outwardly of the third opening of said shell;

said first ring extends over said cutting device so as to be located radially outwardly of the at least one cutting feature; and at least one rib extends downwardly from the inner surface of the shell top section and inwardly from said first ring so as to extend over the at least one cutting feature of said cutting device.

42. The mill head of claim 41, wherein a plurality of said ribs extend inwardly from said first ring.

43. The mill head of claim 41, wherein said shell is formed so that said at least one rib extends downwardly from the inner surface of the shell top section a distance less than the a distance said first ring extends downwardly from the inner surface of said shell top section.

44. The mill head of claim 41, wherein said at least one rib extends linearly inwardly from said first ring.

* * * * *